(12) United States Patent
Sizov

(10) Patent No.: US 11,360,042 B2
(45) Date of Patent: *Jun. 14, 2022

(54) ETHYLENE RECEPTOR BIOSENSOR

(71) Applicant: Strella Biotechnology Company, Wilmington, DE (US)

(72) Inventor: Katherine Konstantin Sizov, Philadelphia, PA (US)

(73) Assignee: Strella Biotechnology Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/338,253

(22) Filed: Jun. 3, 2021

(65) Prior Publication Data
US 2021/0372963 A1    Dec. 2, 2021

Related U.S. Application Data

(63) Continuation of application No. 16/798,377, filed on Feb. 23, 2020, now Pat. No. 11,054,379, which is a
(Continued)

(51) Int. Cl.
*G01N 27/327* (2006.01)
*C07K 14/415* (2006.01)
*A61B 5/1486* (2006.01)
*G01N 27/07* (2006.01)
*G01N 27/404* (2006.01)
(Continued)

(52) U.S. Cl.
CPC ....... *G01N 27/3275* (2013.01); *A61B 5/1486* (2013.01); *C07K 14/415* (2013.01); *G01N 27/07* (2013.01); *G01N 27/3276* (2013.01); *G01N 27/4045* (2013.01); *G01N 33/5302* (2013.01); *G01N 33/5308* (2013.01);
(Continued)

(58) Field of Classification Search
CPC .......... G01N 27/3275; G01N 27/3276; G01N 27/07; G01N 27/4045; G01N 33/02; G01N 33/025; G01N 33/3276; G01N 33/5308; C07K 14/415
See application file for complete search history.

(56) References Cited

U.S. PATENT DOCUMENTS 5,521,101 A * 5/1996 Saini ................... C12Q 1/002
205/777.5
11,054,379 B2 * 7/2021 Sizov ................... A61B 5/1486
(Continued)

OTHER PUBLICATIONS

Chang et al., "*Arabidopsis* Ethylene-Response Gene ETR1: Similarity of Product to Two-Component Regulators," Science vol. 262, Oct. 22, 1993, pp. 539-544 (Year: 1993).*
Chen et al., "Analysis of the functional conservation of ethylene receptors between mainze and *Arabidopsis*," Plant Mol. Biol. (2010) 74:405-421 (Year: 2010).*
Online Ossila article about Cyclic voltammetry, downloaded Feb. 12, 2021 from https://www.ossila.com/pages/cyclic-voltammetry (Year: 2021).*
(Continued)

*Primary Examiner* — Alexander S Noguerola
(74) *Attorney, Agent, or Firm* — Charney IP Law LLC; Thomas M. Finetti

(57) ABSTRACT

The present disclosure relates to biosensors (10) having a receptor layer (5) and a mediator layer (6), the receptor layer including ethylene receptor molecules. The present disclosure also relates to sensor units (20) comprising one or more biosensors (10) and a controller (11). In some embodiments, one or more sensor units (20) may be in wireless communication with a receiver module or a network gateway.

25 Claims, 10 Drawing Sheets

Specification includes a Sequence Listing.

Ethylene Sensor Test in Honey Crisp Apple Controlled Storage Facility

Related U.S. Application Data continuation-in-part of application No. PCT/US2019/032731, filed on May 16, 2019, application No. 17/338,253, which is a continuation of application No. 16/798,377, filed on Feb. 23, 2020, now Pat. No. 11,054,379, which is a continuation of application No. PCT/US2019/062253, filed on Nov. 19, 2019, which is a continuation-in-part of application No. PCT/US2019/032731, filed on May 16, 2019.

(60) Provisional application No. 62/674,639, filed on May 22, 2018.

(51) Int. Cl.
  *G01N 33/53* (2006.01)
  *G01N 33/543* (2006.01)
  *G01N 33/00* (2006.01)
  *G01N 33/02* (2006.01)

(52) U.S. Cl.
  CPC ..... *G01N 33/5438* (2013.01); *G01N 33/0047* (2013.01); *G01N 33/025* (2013.01)

(56) References Cited

U.S. PATENT DOCUMENTS

| | | | |
|---|---|---|---|
| 2003/0108526 A1* | 6/2003 | Sakakibara | C12Q 1/025 424/93.3 |
| 2016/0341709 A1* | 11/2016 | Huang | H04W 4/70 |

OTHER PUBLICATIONS

Mulaudzi et al., "Identification of a novel *Arabidopsis thaliana* nitric oxide-binding molecule with guanylate cyclase activity in vitro," FEBS Letters 585 (2011) 2693-2697 (Year: 2011).*

Hua et al.,"Ethylene Insensitivity Conferred by *Arabidopsis* ERS Gene," Science vol. 269, Sep. 22, 1996, pp. 1712-1714 (Year: 1996).*

Liu et al., "One-step immobilization antibodies using ferrocene-containing thiol aromatic aldehyde for the fabrication of a label-free electrochemical immunosensor," RSC Adv., 2016, 6, 114019 (Year: 2016).*

Entry UniProtKB-P49333 at the UniProt website https://www.uniprot.org/uniprot/P49333, downloaded Nov. 3, 2020 (Sequence last modified Feb. 1, 1996) (Year: 1996).*

Zevenbergen et al., "Electrochemical Sensing of Ethylene Employing a Thin Ionic-Layer," Anal. Chem. Jul. 2011 (Year: 2011).*

* cited by examiner

ETHYLENE RECEPTOR BIOSENSOR

CROSS REFERENCE TO RELATED APPLICATIONS

The present disclosure is a continuation of U.S. patent application Ser. No. 16/798,377 filed on Feb. 23, 2020, which application is a continuation of International Application No. PCT/US19/62253 filed on Nov. 19, 2019, which application claims the benefit of the filing date of International Application No. PCT/US19/32731 filed on May 16, 2019, which application claims the benefit of the filing date of U.S. Provisional Patent Application No. 62/674,639 filed on May 22, 2018; the present disclosure is a continuation of U.S. patent application Ser. No. 16/798,377 filed on Feb. 23, 2020, which application is a continuation-in-part of International Application No. PCT/US19/32731 filed on May 16, 2019, which application claims the benefit of the filing date of U.S. Provisional Patent Application No. 62/674,639 filed on May 22, 2018, the disclosures of which are hereby incorporated by reference herein in their entireties.

BACKGROUND OF THE DISCLOSURE

There is a continuing trend throughout the world toward consumption of fresher and minimally processed food. High quality fresh fruits and vegetables are now available year round, thanks to improved packaging, storage technologies and rapid global transportation. The abundance of year-round fresh produce is dependent on a vast infrastructure including specialized refrigerated storage facilities.

Maintaining the freshness of fruit, vegetables, and other horticultural products, such as fresh cut flowers, is important to the postharvest industry and producers during various stages of transportation and storage. One of the ways to control the freshness of produce is by regulating its exposure to ethylene.

Ethylene is a plant hormone that has a role in many plant development mechanisms. Importantly, it plays a function in the ripening of climacteric fruits in an autocatalytic manner. As fruit ripens, it emits increased concentrations of ethylene, and can be a predictor for the maturity of produce. When produce has a limited exposure to ethylene, its natural aging process will be slowed. Ethylene emissions by fruits, vegetables and flowers occur in a variant-dependent, predictable manner (Watkins 1989; Chu 1984; Chu 1988; Diley 1980; Knee et al. 1983; Perring & Pearson 1986). With a high-accuracy measurement of ethylene, one can predict the stage of ripening and senescence a climacteric fruit is in. Thus, the measurement of ethylene allows for the prediction of ripening before it occurs. This allows for adjustments to be made within the supply chain to prevent food waste. For example, apples are stored in controlled atmosphere (CA) storage rooms for months after they are picked. Determining the proper order in which to pack a CA room for consumption further down the supply chain can minimize food waste and increase produce quality. Such optimization can be performed with a high accuracy ethylene sensor.

The most basic existing technology for ethylene measurement is to obtain an air sample, then later test it at one's convenience for ethylene concentrations under laboratory conditions. For example, an air sample may be gathered in a sample bag and sent to a lab for gas chromatography testing. This technique provides an accurate measurement of ethylene within the conditions of the sample collection. Due to the cumbersome nature of the process, this technique is not practical for continuous ethylene monitoring. One drawback to this technique is that the ethylene concentration is not known in real time—there is a delay associated with the sampling and testing. Additionally, a single sample does not permit for the predictive capabilities ethylene sensing can provide; that is, one cannot make a prediction regarding fruit senescence with infrequent and delayed data points.

Another current technology for ethylene measurement is to use a sampling pump to draw air through a detector tube. When air is pumped over the detector tube, the concentration of a particular gas is indicated. This is normally done by means of a color change shown on graduations along the side of the detection tube. The detection tube can be exposed to air either by means of a hand pump (such as Sensidyne's AP-1S) or by a mechanical pump that draws air more slowly across the detection tube, to provide a reading averaged over a longer period (such as Sensidyne's GilAir5).

The resolution of this technique is only as good as one can read the color change and tends to be accurate within 100 ppm. Such low resolution does not permit for the detection of subtle changes, such as fruit maturity or senescence within the sample. This technique is also limited due to its single-use, disposable tubes.

BRIEF SUMMARY OF THE DISCLOSURE

In one aspect of the present disclosure is a biosensor comprising: (a) a reference electrode including (i) a mediator layer in communication with a base electrode; and (ii) a receptor layer in communication with the mediator layer, wherein the receptor layer comprises an ethylene receptor; and (b) a working electrode in communication with the reference electrode. In some embodiments, the base electrode is comprised of a material selected from the group consisting of copper and silver. In some embodiments, the base electrode comprises a coating of a material selected from the group consisting of copper and gold. In some embodiments, the reference electrode and the working electrode are formed or deposited on the same substrate. In some embodiments, the biosensor further comprises a counter electrode.

In some embodiments, the ethylene receptor is at least 90% identical to a wild-type polynucleotide sequence of an ethylene receptor gene. In some embodiments, the ethylene receptor is at least 95% identical to a wild-type polynucleotide sequence of an ethylene receptor gene. In some embodiments, the ethylene receptor is at least 97% identical to a wild-type polynucleotide sequence of an ethylene receptor gene. In some embodiments, the ethylene receptor is at least 98% identical to a wild-type polynucleotide sequence of an ethylene receptor gene. In some embodiments, the ethylene receptor is at least 99% identical to a wild-type polynucleotide sequence of an ethylene receptor gene. In some embodiments, the ethylene receptor is derived from *Zea mays* or *Arabidopsis*. In some embodiments, the ethylene receptor comprises an amino acid sequence having at least 90% identity to that of SEQ ID NO: 1. In some embodiments, the ethylene receptor comprises an amino acid sequence having at least 90% identity to that of SEQ ID NO: 2. In some embodiments, the ethylene receptor comprises an amino acid sequence having at least 90% identity to that of SEQ ID NO: 3. In some embodiments, the ethylene receptor comprises an amino acid sequence having at least 90% identity to that of SEQ ID NO: 4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a stack comprising: (a) a mediator layer, and (b) a receptor layer in contact with the mediator layer, wherein the receptor layer comprises an ethylene receptor protein. In some embodiments, the ethylene receptor protein has an amino acid sequence having at least 95% identity to any of the ethylene receptor proteins selected from the group consisting of ETR1, ETR2, ETR3, and ETR4. In some embodiments, the ethylene receptor protein is selected from the group consisting of ETR1, ETR2, ETR3, and ETR4. In some embodiments, the ethylene receptor protein comprises an amino acid sequence having at least 85% identity to any one of SEQ ID NOS: 1-4. In some embodiments, the ethylene receptor protein comprises an amino acid sequence having at least 90% identity to any one of SEQ ID NOS: 1-4. In some embodiments, the ethylene receptor protein comprises an amino acid sequence having at least 95% identity to any one of SEQ ID NOS: 1-4. In some embodiments, the ethylene receptor protein comprises an amino acid sequence having at least 96% identity to any one of SEQ ID NOS: 1-4. In some embodiments, the ethylene receptor protein comprises an amino acid sequence having at least 97% identity to any one of SEQ ID NOS: 1-4. In some embodiments, the ethylene receptor protein comprises an amino acid sequence having at least 98% identity to any of SEQ ID NOS: 1-4. In some embodiments, the ethylene receptor protein comprises an amino acid sequence having at least 99% identity to any one of SEQ ID NOS: 1-4. In some embodiments, the ethylene receptor protein comprises an amino acid sequence having any one of SEQ ID NOS: 1-4. In some embodiments, between about 0.0005 mg/mm to about 1.75 mg/mm of ethylene receptor are protein are included within the receptor layer. In some embodiments, between about 0.0008 mg/mm to about 1.55 mg/mm of ethylene receptor are protein are included within the receptor layer. In some embodiments, between about 0.1 to about 0.8 mg/mm of ethylene receptor are protein are included within the receptor layer. In some embodiments, between about 0.9 to about 1.6 mg/mm of ethylene receptor are protein are included within the receptor layer. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a reference electrode comprising a stack deposited on a base electrode, wherein the stack comprises (a) a mediator layer, and (b) a receptor layer in contact with the mediator layer, wherein the receptor layer comprises an ethylene receptor protein. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the ethylene receptor protein comprises an amino acid sequence having at least 95% identity to any one of SEQ ID NOS: 1-4. In some embodiments, the ethylene receptor protein comprises an amino acid sequence having at least 96% identity to any one of SEQ ID NOS: 1-4. In some embodiments, the ethylene receptor protein comprises an amino acid sequence having at least 97% identity to any one of SEQ ID NOS: 1-4. In some embodiments, the ethylene receptor protein comprises an amino acid sequence having at least 98% identity to any one of SEQ ID NOS: 1-4. In some embodiments, the ethylene receptor protein comprises an amino acid sequence having at least 99% identity to any one of SEQ ID NOS: 1-4. In some embodiments, the ethylene receptor protein comprises an amino acid sequence having any one of SEQ ID NOS: 1-4. In some embodiments, between about 0.0005 mg/mm to about 1.75 mg/mm of ethylene receptor are protein are included within the receptor layer. In some embodiments, between about 0.0008 mg/mm to 1.55 mg/mm of ethylene receptor are protein are included within the receptor layer. In some embodiments, between about 0.1 to about 0.8 mg/mm of ethylene receptor are protein are included within the receptor layer. In some embodiments, between about 0.9 to about 1.6 mg/mm of ethylene receptor are protein are included within the receptor layer. In some embodiments, the base electrode is a metal electrode. In some embodiments, the metal electrode is comprised of copper or silver. In some embodiments, the base electrode comprises a coating including copper or silver. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a biosensor comprising (i) a reference, and; and (ii) a working electrode in communication with the reference electrode; wherein the reference electrode comprises a stack deposited on a metal electrode, wherein the stack comprises (a) a mediator layer, and (b) a receptor layer in contact with the mediator layer, wherein the receptor layer comprises an ethylene receptor protein. In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the reference electrode and the working electrode are both formed or deposited on the same substrate. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a sensor unit comprising (i) one or more biosensors, and (ii) a controller in communication with the one or more biosensors; wherein the biosensor includes a reference electrode in communication with a working electrode, the reference electrode having a stack deposited on an electrode, wherein the stack includes (a) a mediator layer, and (b) a receptor layer in contact with the mediator layer, wherein the receptor layer comprises an ethylene receptor protein. In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole. In some embodiments, the controller comprises a communication module. In some embodiments, the communication module is a wireless communication module.

In another aspect of the present disclosure is a sensor unit comprising (1) one or more biosensors, and (2) a controller in communication with the one or more biosensors; wherein the biosensor includes (a) a reference electrode including (i) a mediator layer deposited on a metal electrode; and (ii) a receptor layer deposited on the mediator layer, wherein the receptor layer comprises an ethylene receptor; and (b) a working electrode in communication with the reference electrode. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole. In some embodiments, the controller comprises a communication module. In some embodiments, the communication module is a wireless communication module.

In another aspect of the present disclosure is a system comprising a plurality of the sensor units described above, wherein the plurality of sensor units are each independently in wireless communication with a receiver module, a gateway, or a storage module.

In another aspect of the present disclosure is a container comprising at least one of the sensor units described above. In some embodiments, each container is in wireless communication with a receiver module, a gateway, or a storage module.

In another aspect of the present disclosure is a method of detecting the presence of ethylene using any of the biosensors or sensor units described above. In some embodiments, a quantitative measurement of an ethylene concentration may be made using any of the biosensors or sensor units described above.

In another aspect of the present disclosure is a biosensor comprising: (a) a reference electrode including (i) a mediator layer in communication with a base electrode; and (ii) a receptor layer in communication with the mediator layer, wherein the receptor layer comprises an ethylene receptor; (b) a working electrode in communication with the reference electrode; and (c) a counter electrode. In some embodiments, the base electrode is comprised of a material selected from the group consisting of copper and silver. In some embodiments, the base electrode comprises a coating of a material selected from the group consisting of copper and gold. In some embodiments, the reference electrode and the working electrode are formed or deposited on the same substrate.

In some embodiments, the ethylene receptor is at least 90% identical to a wild-type polynucleotide sequence of an ethylene receptor gene. In some embodiments, the ethylene receptor is at least 95% identical to a wild-type polynucleotide sequence of an ethylene receptor gene. In some embodiments, the ethylene receptor is at least 97% identical to a wild-type polynucleotide sequence of an ethylene receptor gene. In some embodiments, the ethylene receptor is at least 98% identical to a wild-type polynucleotide sequence of an ethylene receptor gene. In some embodiments, the ethylene receptor is at least 99% identical to a wild-type polynucleotide sequence of an ethylene receptor gene. In some embodiments, the ethylene receptor is derived from *Zea mays* or *Arabidopsis*. In some embodiments, the ethylene receptor comprises an amino acid sequence having at least 90% identity to that of SEQ ID NO: 1. In some embodiments, the ethylene receptor comprises an amino acid sequence having at least 90% identity to that of SEQ ID NO: 2. In some embodiments, the ethylene receptor comprises an amino acid sequence having at least 90% identity to that of SEQ ID NO: 3. In some embodiments, the ethylene receptor comprises an amino acid sequence having at least 90% identity to that of SEQ ID NO: 4. In some embodiments, the mediator layer comprises at least one of potassium ferricyanide, methyl viol ogen, ferrocene, cysteamine, mercaptopropionic acid, mercaptobenzoic acid, mercaptoundecanoic acid, ruthenium chloride, naphthol green, or polypyrrole.

In another aspect of the present disclosure is a biosensor comprising (i) a reference, and; (ii) a counter electrode; and (iii) a working electrode in communication with the reference electrode; wherein the reference electrode comprises a stack deposited on a metal electrode, wherein the stack comprises (a) a mediator layer, and (b) a receptor layer in contact with the mediator layer, wherein the receptor layer comprises an ethylene receptor protein. In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the reference electrode and the working electrode are both formed or deposited on the same substrate. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

In another aspect of the present disclosure is a sensor unit comprising (i) one or more biosensors, and (ii) a controller in communication with the one or more biosensors; wherein the biosensor includes a counter electrode, and reference electrode in communication with a working electrode, the reference electrode having a stack deposited on an electrode, wherein the stack includes (a) a mediator layer, and (b) a receptor layer in contact with the mediator layer, wherein the receptor layer comprises an ethylene receptor protein. In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole. In some embodiments, the controller comprises a communication module. In some embodiments, the communication module is a wireless communication module.

In another aspect of the present disclosure is a sensor unit comprising (1) one or more biosensors, and (2) a controller in communication with the one or more biosensors; wherein the biosensor includes (a) a reference electrode including (i) a mediator layer deposited on a metal electrode; and (ii) a receptor layer deposited on the mediator layer, wherein the receptor layer comprises an ethylene receptor; (b) a working electrode in communication with the reference electrode; and (c) a counter electrode. In some embodiments, the ethylene receptor protein is selected from the group consisting of ETR1, ETR2, ETR3, and ETR4. In some embodiments, the ethylene receptor protein comprises an amino acid sequence having at least 90% identity to any of SEQ ID NOS: 1-4. In some embodiments, the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole. In some embodiments, the controller comprises a communication module. In some embodiments, the communication module is a wireless communication module.

In another aspect of the present disclosure is a system comprising a plurality of the sensor unit, including any sensor unit incorporating a three-electrode design, wherein the plurality of sensor units are each independently in wireless communication with a receiver module, a gateway, or a storage module.

In another aspect of the present disclosure is a container comprising at least one of the sensor units described above, including any sensor unit incorporating a three-electrode design. In some embodiments, each container is in wireless communication with a receiver module, a gateway, or a storage module.

In another aspect of the present disclosure is a method of detecting the presence of ethylene using any of the biosensors or sensor units described above, including any biosensor or sensor unit incorporating a three-electrode design. In some embodiments, a quantitative measurement of an ethylene concentration may be made using any of the biosensors or sensor units described above.

SEQUENCE LISTING

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "Strella-002WO_ST25.txt" created on May 7, 2019, 27 kb, which is incorporated by reference herein.

BRIEF DESCRIPTION OF THE FIGURES

For a general understanding of the features of the disclosure, reference is made to the drawings. In the drawings, like reference numerals have been used throughout to identify identical elements.

DETAILED DESCRIPTION

Figure 1:
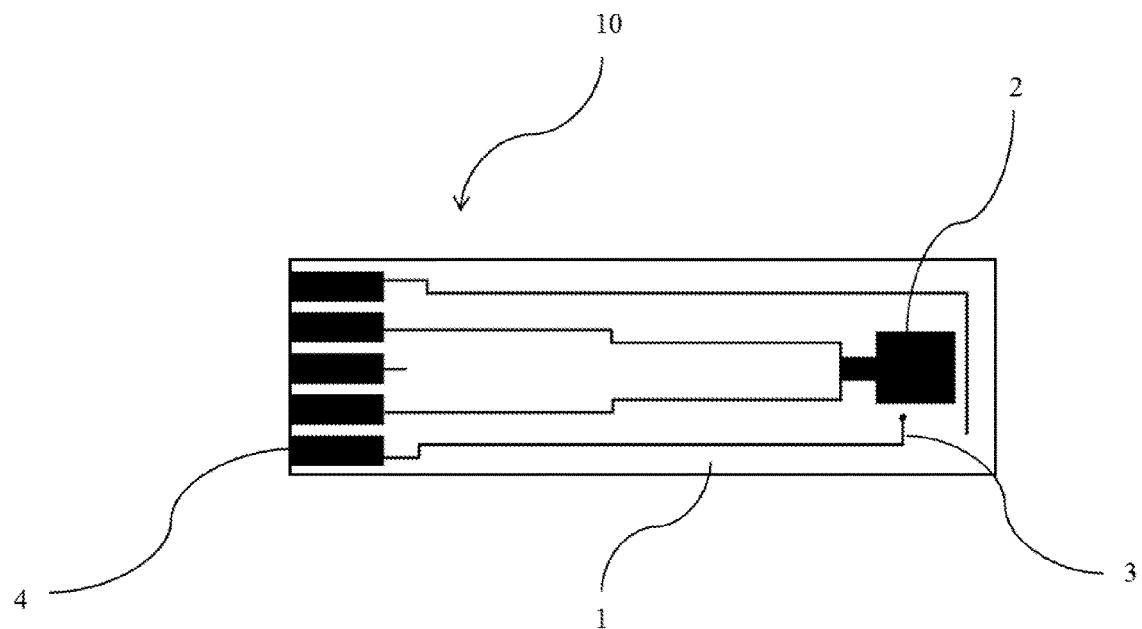
FIG. 1 illustrates a top down view of a biosensor in accordance with one embodiment of the present disclosure.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of" when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The present disclosure is directed to a biosensor comprising a reference electrode and a working electrode, wherein the reference electrode includes a layer comprising ethylene receptor molecules.

FIG. 1 depicts a top-down view of a biosensor 10 in accordance with one embodiment of the present disclosure. In some embodiments, the biosensor 10 includes a reference electrode 2 and a working electrode 3. In some embodiments, the reference electrode 2 and the working electrode 3 are provided on substrate 1. In some embodiments, substrate 1 is a non-conductive substrate, such as a fiberglass epoxy resin or a phenolic resin. In some embodiments, the substrate is selected from carbon, fiberglass epoxy resin, phenolic resin, insulated metal substrate, polyimide film and fluoropolymer/polyimide film composites. In some embodiments, the biosensor 10 further comprises one or more leads, so as to allow the biosensor to communicate with other components and/or devices. In some embodiments, the leads are comprised of conductive tracks within the substrate, connecting to the reference electrode surface and the working electrode. In some embodiments, the leads are comprised of the same metal in which the electrode is comprised. In some embodiments, the biosensor depicted in FIG. 1 includes one or more additional traces or leads.

Figure 8:
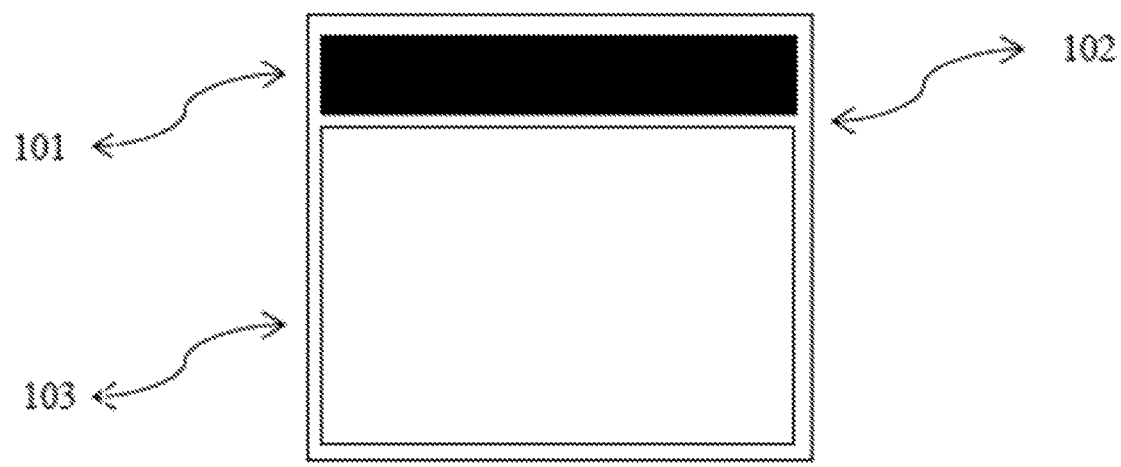
FIG. 8 illustrates a two-electrode system in accordance with one embodiment of the present disclosure.

FIG. 8 sets forth a top down schematic of a two-electrode system in accordance with one embodiment of the present disclosure. In some embodiments, a reference electrode 101 having a metal composition which differs from the working electrode 103 is separated by a gap 102. In some embodiments, an electrolytic mediator layer is posited proximal (e.g. atop) the two electrodes. Without wishing to be bound by any particular theory, it is believed that the electrolytic mediator layer promotes electron transfer between the reference electrode 101 and the working electrode 103. In some embodiments, and upon a reaction between the ethylene receptor and ethylene (such as described herein), an oxidation reduction reaction catalyzes the movement of electrons from one electron to the other, which can be measured via current or voltage changes.

Figure 9:
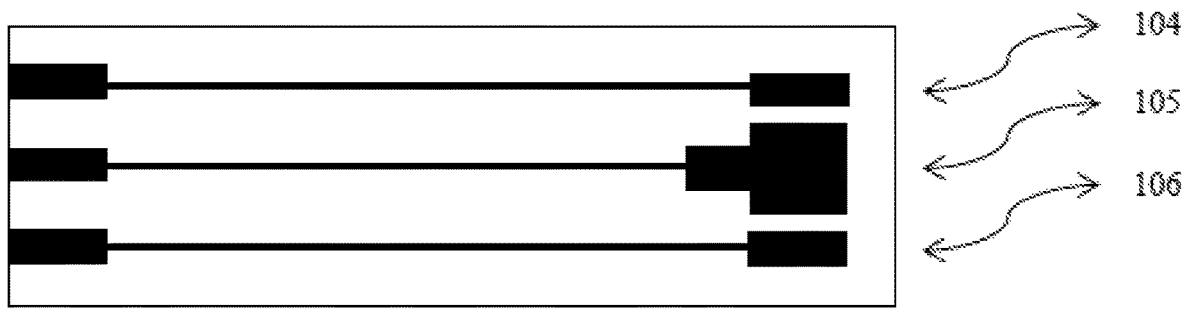
FIG. 9 illustrates a three-electrode system in accordance with the present disclosure.

FIG. 9 sets forth a top down schematic of a three-electrode system in accordance with another embodiment of the present disclosure. In some embodiments, the three-electrode system consists of three electrodes: a counter electrode 105, a reference electrode 104, and a working electrode 106. In some embodiments, the counter electrode 105 includes an ethylene receptor protein (including any of those described herein). In some embodiments, it is believed that the ethylene receptor protein undergoes a reduction and oxidation reaction upon contact with one or more ethylene molecules, such as those ethylene molecules present in an environment (e.g. an environment surrounding the biosensor). In some embodiments, this is believed to generate an electrical potential between the counter electrode 105 and the working electrode 106. In some embodiments, an electrolytic mediator layer is positioned proximal (e.g. atop) the two electrodes and is believed to promote electron transfer between the counter and working electrodes 105 and 106, respectively. In some embodiments, the measured current is believed to pass through the counter electrode and the third electrode, the working electrode. In some embodiments, an electrolytic solution in the form of the mediator layer is in contact (e.g. placed between) at least two of the electrodes, e.g. all three of the electrodes, to provide ions to the electrodes during the oxidation and reduction reaction between ethylene and the ethylene receptor protein.

In some embodiments, a three-electrode system permits stability advantages over the two-electrode system. With three electrodes, one can supply an external potential to the system, eliminating a variable. Theoretically, in a two-electrode system, ions are supplied due to galvanic corrosion of the two electrodes. In some embodiments, the potential generated between the two electrodes permits the reaction of ethylene with ethylene receptor. However, it is difficult to control this ion supply, and thus the design of the two-electrode system presents greater stability issues than that of the three-electrode system. In some embodiments, the measurable output of a two-electrode system tends to be either voltage or resistance. Due to the variable nature of electron supply to the system, factors such as the external environment are more likely to affect the outputs of the system.

In a three-electrode system, potential is supplied by one of the three electrodes, typically the reference electrode. Thus, there is a measurable quantity of ions supplied to the electrode system, and thus a stable baseline reading, typically of resistance. As such, any resistance change in the system is likely due to the binding event between ethylene and the ethylene receptor, generating a cleaner and more decipherable signal."

Figure 2A:
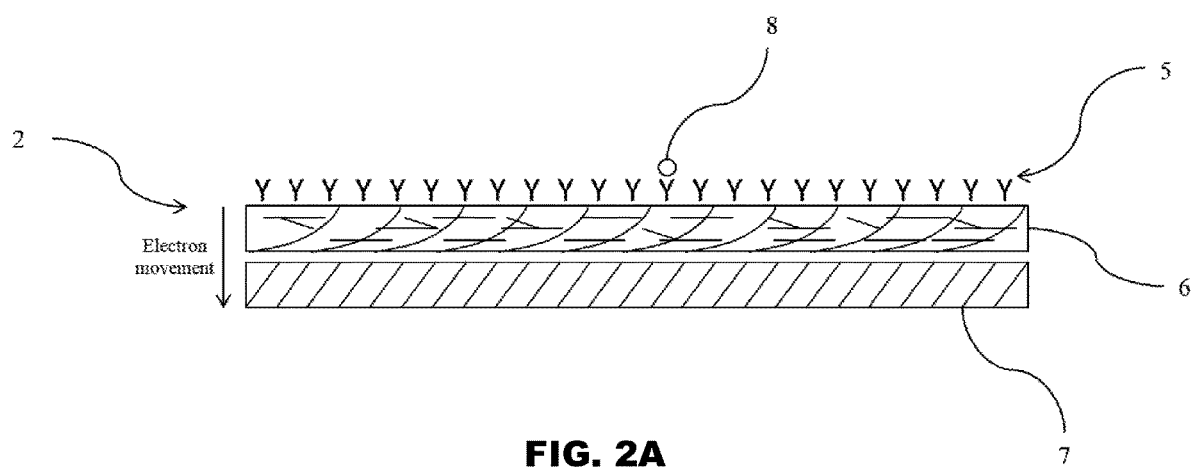
FIG. 2A illustrates a side view of a reference electrode in accordance with one embodiment of the present disclosure.

In some embodiments, and with reference to FIG. 2A, the reference electrode 2 comprises a receptor layer 5, a mediator layer 6, and a base electrode 7. The base electrode 7 may be comprised of any material known to those of ordinary skill in the art. For example, the base electrode 7 may be comprised of copper, gold, aluminum, or silver. In some embodiments, the base the electrode 7 may be comprised of indium tin oxide, gold, or silver electrodes. In some embodiments, the electrode 7 comprises a conductive metallic coating. In some embodiments, the metallic coating comprises copper and/or silver.

Figure 2B:
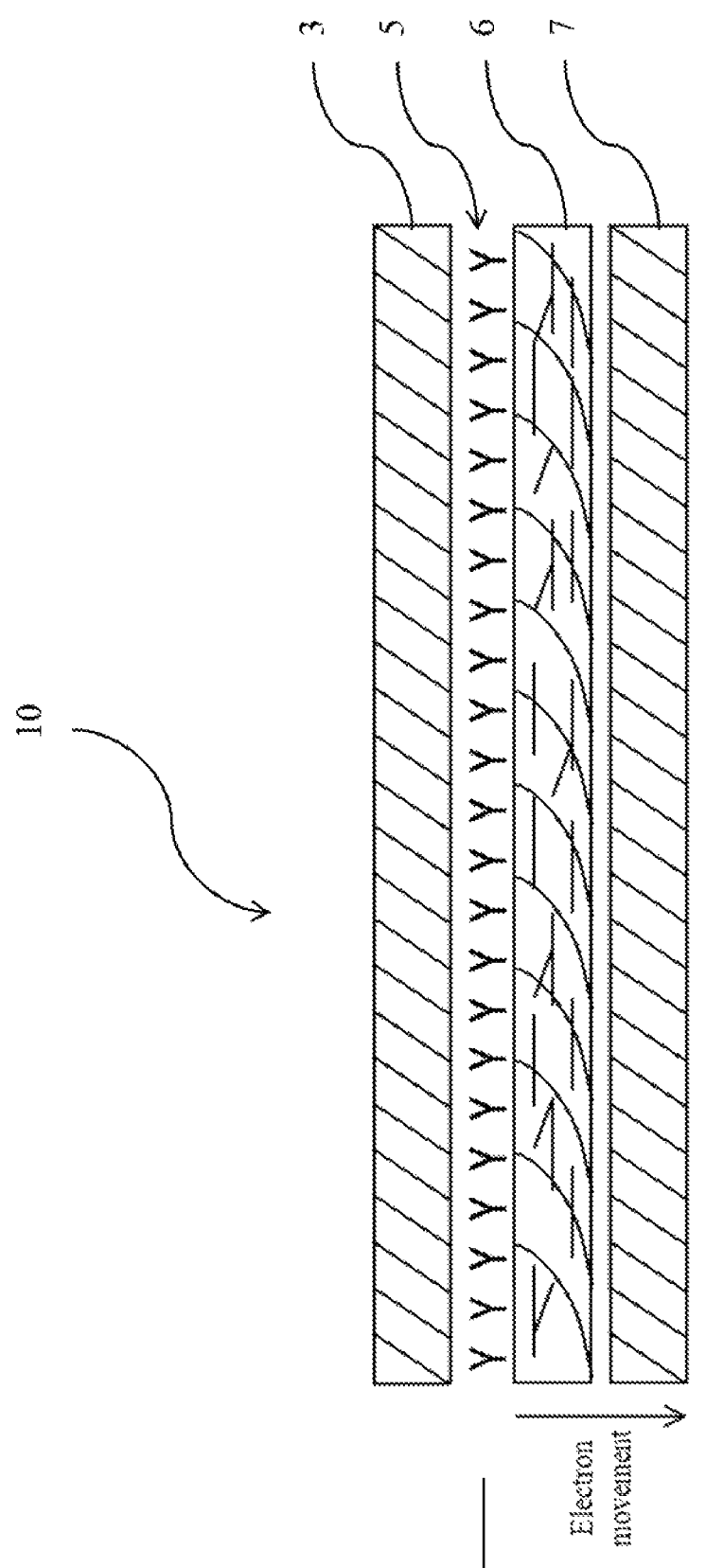
FIG. 2B illustrates a side view of a biosensor in accordance with another embodiment of the present disclosure.

FIG. 2B illustrates an alternative biosensor 10 having a reference electrode 2 including a receptor layer 5, a mediator layer 6, and an electrode 7. The biosensor depicted in FIG. 2B further includes a working electrode 3 in communication with the receptor layer 5. In some embodiments, the working electrode 3 is comprised of a material selected from gold, silver, copper, or any combination thereof. In some embodiments, the working electrode 3 of FIG. 2B is comprised of a porous material, such as metal triazolates consisting of 1H-1,2,3-triazole and divalent metal ions (Mg, Mn, Fe, Co, Cu, and Zn). In other embodiments, the working electrode of FIG. 2B includes one or more pores or punctures to facilitate the permeation of the ethylene gas through the working electrode layer 3 and to the receptor layer 5. In some embodiments, the pores or punctures may have a radius ranging from between about 2 angstroms to about 2 mm.

In some embodiments, the mediator layer 6 comprises a conductive and biocompatible material that serves to mediate electron transfer between the receptor layer and the metallic electrode. It is also believed that the mediator layer 6 serves to stabilize the components of the receptor layer, described herein. It is further believed that the mediator layer 6 facilitates crosslinking interactions with ethylene receptor proteins such that the ethylene receptor proteins become immobilized on the surface of the mediator layer 6. It is believed that electron movement resulting from reversible chemical interactions between ethylene and ethylene receptor molecules is encouraged due to the conductivity, and subsequent voltage output (between about 0 to about 7V), of the mediator layer.

In some embodiments, the mediator layer 6 comprises at least one component selected from potassium ferricyanide, ferric chloride, methyl viologen, ferrocene, cysteamine, mercaptopropionic acid, mercaptobenzoic acid, mercaptoundecanoic acid, ruthenium chloride, naphthol green, or polypyrrole. In some embodiments, the mediator layer 6 comprises (i) a first component selected from potassium ferricyanide, ferric chloride, methyl viologen, ferrocene, cysteamine, mercaptopropionic acid, mercaptobenzoic acid, mercaptoundecanoic acid, ruthenium chloride, naphthol green, or polypyrrole; and (ii) a second component.

In some embodiments, the mediator layer 6 comprises the components set forth in Table 1 below.

Table 1 provides a listing of mediator layers which may be utilized and the components of each of those mediator layers.

| Name of layer | Composition |
| --- | --- |
| Prussian Blue | about 0.05M potassium ferricyanide $3Fe(CN)_6$ and about 0.05M ferric chloride both in about 5 mmol $L^{-1}$ HCl |
| Methyl Viologen | about 10 µL glycerol, about 5 microliter nafion, about 20 microliter enzyme solution, about 10% w/v methyl viologen in about 20 mM 7.4 PBS, reticulated in saturated glutaraldehyde vapor |
| Ferrocene | about 1% (w/w) Nafion solution (in EtOH), about 0.05M ferrocene solution in DI water, about 5 mg/mL ethylene receptor solution, about 4 microliters/mL glutaraldehyde solution (25%, aqueous) |
| Cysteamine | between about 1.2 to about 2.9M cysteamine, about 2 mg/ml of enzyme |
| 3-mercaptopropionic acid | about 1.2M 3-mercaptopropionic acid, about 30 mM EDC and about 15 mM NHS, about 5 mg/mL ethylene receptor solution |

| Name of layer | Composition |
| --- | --- |
| 4-mercaptobenzoic acid | about 1.2M 4-mercaptobenzoic acid solution, about 30 mM EDC and about 15 mM NHS, about 5 mg/mL ethylene receptor solution |
| 11-mercaptoundecanoic acid | about 1.2M 11-mercaptoundecanoic acid, about 30 mM EDC and about 15 mM NHS, 5 mg/mL ethylene receptor solution |
| Ruthenium purple | about 1 mM of RuCl3 solution including about 1 mM KCl |
| Naphthol Green B | about 4 mmol/L naphthol green, about 3 mg/mL ethylene receptor solution |
| (Os-(bpy)FecI I) | about 8-µL of a 6-mg/ml (Os(bpy)2PVI), about 1.9 µL of a about 15-mg/mL aqueous solution of PEGDGE and about 4.8 µL of 10-mg/ml ethylene solution |
| Polypyrrole | PVDF granules in DMF (about 2% W/V) added to $FeCl_3$ to which about 2% polypyrrole is added |

In some embodiments, the receptor layer 5 comprises an ethylene receptor protein. The term "ethylene receptor" or "ethylene receptor protein," refers to ethylene receptors from any of the ethylene receptor families present in a plant. By way of example, in *Arabidopsis*, ethylene receptor proteins include ETR1, ERS1, ETR2, ERS2, and EIN4. *Zea mays* ethylene receptor proteins include ZmERS1 and ZmETR2 (including the ZmETR2 variants ZmETR9 and ZmETR40). In some embodiments, the ethylene receptor proteins are derived from the genes of *Lactuca Sativa*, Bryophyta, *Petunia*, and *Solanum lycopersicum* may also be used. Methods of isolating ethylene receptors are described herein, and also described in U.S. Pat. Nos. 7,951,993 and 7,105,654, the disclosures of which are hereby incorporated by reference herein in their entireties.

Ethylene receptors of the present disclosure may be isolated from any species of plant and include species homologs of the exemplary ethylene receptors. In that regard, in some embodiments, the ethylene receptor protein is naturally occurring. Examples of naturally occurring ethylene receptors include ethylene receptor 1 (ETR1) (such as derived from *ARABIDOPSIS THALIANA*), ethylene receptor 2 (ETR 2) (such as derived from *ARABIDOPSIS THALIANA*), ethylene receptor 3 (ETR3) (such as derived from *ORYZA SATIVA* INDICA), or ethylene receptor 4 (ETR4) (such as derived from *ORYZA SATIVA JAPONICA*).

In some embodiments, the ethylene receptor protein comprises a nucleotide sequence which is at least 90% identical to a wild-type polynucleotide sequence of an ethylene receptor gene. In some embodiments, the ethylene receptor protein comprises a nucleotide sequence which is at least 95% identical to a wild-type polynucleotide sequence of an ethylene receptor gene. In some embodiments, the ethylene receptor protein comprises a nucleotide sequence which is at least 97% identical to a wild-type polynucleotide sequence of an ethylene receptor gene. In some embodiments, the ethylene receptor protein comprises a nucleotide sequence which is at least 98% identical to a wild-type polynucleotide sequence of an ethylene receptor gene. In some embodiments, the ethylene receptor protein comprises a nucleotide sequence which is at least 99% identical to a wild-type polynucleotide sequence of an ethylene receptor gene.

In some embodiments, the ethylene receptor has at least 80% identity to the amino acid sequence of SEQ ID NO: 1. In some embodiments, the ethylene receptor has at least 85% identity to the amino acid sequence of SEQ ID NO: 1. In some embodiments, the ethylene receptor has at least 90% identity to the amino acid sequence of SEQ ID NO: 1. In some embodiments, the ethylene receptor has at least 95% identity to the amino acid sequence of SEQ ID NO: 1. In some embodiments, the ethylene receptor has at least 96% identity to the amino acid sequence of SEQ ID NO: 1. In some embodiments, the ethylene receptor has at least 97% identity to the amino acid sequence of SEQ ID NO: 1. In some embodiments, the ethylene receptor has at least 98% identity to the amino acid sequence of SEQ ID NO: 1. In some embodiments, the ethylene receptor has at least 99% identity to the amino acid sequence of SEQ ID NO: 1. In some embodiments, the ethylene receptor comprises the amino acid sequence of SEQ ID NO: 1.

In some embodiments, the ethylene receptor has at least 80% identity to the amino acid sequence of SEQ ID NO: 2. In some embodiments, the ethylene receptor has at least 85% identity to the amino acid sequence of SEQ ID NO: 2. In some embodiments, the ethylene receptor has at least 90% identity to the amino acid sequence of SEQ ID NO: 2. In some embodiments, the ethylene receptor has at least 95% identity to the amino acid sequence of SEQ ID NO: 2. In some embodiments, the ethylene receptor has at least 96% identity to the amino acid sequence of SEQ ID NO: 2. In some embodiments, the ethylene receptor has at least 97% identity to the amino acid sequence of SEQ ID NO: 2. In some embodiments, the ethylene receptor has at least 98% identity to the amino acid sequence of SEQ ID NO: 2. In some embodiments, the ethylene receptor has at least 99% identity to the amino acid sequence of SEQ ID NO: 2. In some embodiments, the ethylene receptor comprises the amino acid sequence of SEQ ID NO: 2.

In some embodiments, the ethylene receptor has at least 80% identity to the amino acid sequence of SEQ ID NO: 3. In some embodiments, the ethylene receptor has at least 85% identity to the amino acid sequence of SEQ ID NO: 3. In some embodiments, the ethylene receptor has at least 90% identity to the amino acid sequence of SEQ ID NO: 3. In some embodiments, the ethylene receptor has at least 95% identity to the amino acid sequence of SEQ ID NO: 3. In some embodiments, the ethylene receptor has at least 96% identity to the amino acid sequence of SEQ ID NO: 3. In some embodiments, the ethylene receptor has at least 97% identity to the amino acid sequence of SEQ ID NO: 3. In some embodiments, the ethylene receptor has at least 98% identity to the amino acid sequence of SEQ ID NO: 3. In some embodiments, the ethylene receptor has at least 99% identity to the amino acid sequence of SEQ ID NO: 3. In some embodiments, the ethylene receptor comprises the amino acid sequence of SEQ ID NO: 3.

In some embodiments, the ethylene receptor has at least 80% identity to the amino acid sequence of SEQ ID NO: 4.

In some embodiments, the ethylene receptor has at least 85% identity to the amino acid sequence of SEQ ID NO: 4. In some embodiments, the ethylene receptor has at least 90% identity to the amino acid sequence of SEQ ID NO: 4. In some embodiments, the ethylene receptor has at least 95% identity to the amino acid sequence of SEQ ID NO: 4. In some embodiments, the ethylene receptor has at least 96% identity to the amino acid sequence of SEQ ID NO: 4. In some embodiments, the ethylene receptor has at least 97% identity to the amino acid sequence of SEQ ID NO: 4. In some embodiments, the ethylene receptor has at least 98% identity to the amino acid sequence of SEQ ID NO: 4. In some embodiments, the ethylene receptor has at least 99% identity to the amino acid sequence of SEQ ID NO: 4. In some embodiments, the ethylene receptor comprises the amino acid sequence of SEQ ID NO: 4.

In other embodiments, the ethylene receptors also include proteins with naturally-occurring and induced mutations, including insertion, deletion, and point mutations. In yet other embodiments, the ethylene receptor protein is non-naturally occurring.

In some embodiments, between about 10 to about 1000 nanograms of ethylene receptor are protein are included within the receptor layer. In some embodiments, between about 20 to about 600 nanograms of ethylene receptor protein is included within the receptor layer. In some embodiments, between about 50 to about 300 nanograms of ethylene receptor protein is included within the receptor layer. In some embodiments, about 0.015 milligrams of ethylene receptor protein applied for every cubic centimeter of the components of the mediator layer applied. In some embodiments, about 0.04 milligrams of ethylene receptor protein are applied for every cubic centimeter of the components of the mediator layer applied. In some embodiments, about 0.002 milligrams of ethylene receptor protein are applied for every cubic centimeter of the components of the mediator layer applied.

In some embodiments, the overall thickness of the reference electrode ranges from between about 0.1 mm to about 1.5 mm. In some embodiments, each of the individual layers of the reference electrode do not exceed about 1 mm in thickness.

The ethylene receptors described above may be isolated and collected according to any process known to those of ordinary skill in the art. For example, ethylene receptor production may include the steps of (1) expressing ethylene-binding proteins in a vector host; (2) amplifying vector hosts to desired volumes; and (3) extracting/isolating desired proteins from the vector hosts. In some embodiments, gene sequences for proteins capable of binding to ethylene are expressed within a plasmid capable of being expressed by the vector host. Vector hosts are typically prokaryotic cells but may also include eukaryotic cells as well. The plasmid within which the gene sequence is inserted must be able to be translated by the vector host. Upon successful insertion of the plasmid into the vector host, the host is amplified. In bacteria, amplification typically involves culturing bacterial hosts within a broth solution for about 8 to about 12 hours. Following incubation of bacterial host with broth, the resulting bacteria is centrifuged, and protein isolation methods are performed. The means of protein extraction can be chemical, through the means of a detergent, or mechanical, such as sonication or heat treatments. An alternative means of protein extraction is by attaching a specific tag to the plasmid, such as a histidine tag, and using a column to purify his-tagged proteins. Other methods of isolating and collecting ethylene receptors are described in U.S. Patent Publication Nos. 2002/0012982A1 and US20020127587A1; U.S. Pat. Nos. 4,431,739, 4,366,246, and 3,585,179; and also, in EP0001929B1 and EP0001929A2, the disclosures of which are hereby incorporated by reference herein in their entireties.

Without wishing to be bound by any particular theory, it is believed that when an ethylene gas molecule 8 binds to the ethylene receptor molecules within the receptor layer 5, electron transfer occurs (see FIGS. 2A and 2B, where an ethylene molecule 8 is bound to an ethylene receptor in the receptor layer 5). In the case of the presently disclosed biosensors, the electron transfer may be passed from the receptor layer 5 to the mediator layer 6 and ultimately to the electrode 7 (see FIGS. 2A and 2B). It is further believed that multiple binding events generate electron movement that can be measured as a voltage change. The resulting voltage change can be linearly correlated to the concentration of atmospheric ethylene. It is believed that the correlation can be made by exposing the ethylene sensor to a standard of known ethylene gas concentrations and measuring the resulting voltage output. For example, over the course of a period of time, one can expose the ethylene sensor to increasing parts per million of ethylene and measure the change in voltage. These data points can then be used to estimate a linear equation correlating voltage output to ethylene binding to the sensor and resulting air concentrations of ethylene.

The biosensor 10 may be fabricated according to any method known to those of ordinary skill in the art. In some embodiments, a solution comprising the desired components of the mediator layer are drop coated onto an electrode 7 or a coated electrode 7. The components of any mediator layer 6 and the concentrations of those components relative to each other are described above in Table 1. Following the deposition of the mediator layer 6, the receptor layer 5 may be drop coated onto the mediator layer. In some embodiments, the ethylene receptor protein is included within a buffer solution and the solution is applied to a dried mediator layer 5 to provide the receptor layer 6 (upon its drying). The receptor solution typically consists of a solution with a pH range of about 7 to about 9 for the lysis of proteins. A typical lysis buffer solution contains about 50 to about 100 mM Tris-HCl, about 100 to about 300 mM NaCl, about 1 mM Dithiothreitol (DTT) or about 1% NP-40. Additionally, protease inhibitors or protease inhibitor cocktails may be added to the buffer solution following protein lysis. Alternative buffer solutions are shown in Table 2.

Table 2 lists various buffers and their corresponding pKa values. Any of the ethylene receptor proteins described herein may be provided in solution with any of the buffers of Table 2.

| Buffer | pKa at 20° C. |
|---|---|
| MES | 6.15 |
| Bis-tris methane | 6.60 |
| ADA | 6.62 |
| N-(2-Acetamido)-2-aminoethanesulfonic acid (ACES) | 6.76 |
| Bis-tris propane | 6.80 |
| piperazine-N,N'-bis(2-ethanesulfonic acid) (PIPES) | 6.82 |
| 3-Morpholino-2-hydroxypropanesulfonic acid (MOPSO) | 6.95 |
| Cholamine chloride | 7.10 |
| 3-(N-morpholino)propanesulfonic acid (MOPS) | 7.15 |
| bis(2-hydroxyethyl)amine (BES) | 7.17 |
| 2-[[1,3-dihydroxy-2-(hydroxymethyl)propan-2-yl]amino]ethanesulfonic acid (TES) | 7.5 |

-continued

| Buffer | pKa at 20° C. |
|---|---|
| (4-(2-hydroxyethyl)-1-piperazineethanesulfonic acid) (HEPES) | 7.55 |
| [3-Bis(2-hydroxyethyl) amino-2-hydroxypropane-1-sulfonic acid] (DIPSO) | 7.6 |
| 4-(N-Morpholino)butanesulfonic acid (MOBS) | 7.6 |
| Acetamidoglycine | 7.7 |
| 3-[[1,3-dihydroxy-2-(hydroxymethyl)propan-2-yl]amino]-2-hydroxypropane-1-sulfonic acid (TAPSO) | 7.6 |
| tris(hydroxymethyl)aminomethane-acetate-Ethylenediaminetetraacetic acid (TEA) | 7.8 |
| [Piperazine-1,4-bis(2-hydroxy-3-propanesulfonic acid),dihydrate] (POPSO) | 7.85 |
| ((2-Hydroxyethyl)-piperazine-N-2-hydroxypropanesulfonic acid) (HEPPSO) | 7.9 |
| EPS | 8.0 |
| 3-[4-(2-Hydroxyethyl)piperazin-1-yl]propane-1-sulfonic acid (HEPPS) | 8.1 |
| N-(2-Hydroxy-1,1-bis(hydroxymethyl)ethyl)glycine (Tricine) | 8.15 |
| tris(hydroxymethyl)aminomethane | 8.2 |
| Glycinamide | 8.2 |
| Glycylglycine | 8.2 |
| N-(2-Hydroxyethyl)piperazine-N'-(4-butanesulfonic acid) (HEPBS) | 8.3 |
| 2-(Bis(2-hydroxyethyl)amino)acetic acid (Bicine) | 8.35 |
| 3-{[1,3-dihydroxy-2-(hydroxymethyl)propan-2-yl]amino}propane-1-sulfonic acid (TAPS) | 8.55 |
| 2-Amino-2-Methyl-1-Propanol (AMP) | 8.8 |
| 2-(Cyclohexylamino)ethanesulfonic acid (CHES) | 9.3 |
| ((1,1-Dimethyl-2-hydroxyethyl)amino)-2-hydroxypropanesulfonic acid sodium salt (AMPSO) | 9.0 |
| N-cyclohexyl-2-hydroxyl-3-aminopropanesulfonic acid (CAPSO) | 9.6 |
| 3-(Cyclohexyl amino)-1-propanesulfonic acid (CAPS) | 10.4 |

Figure 3A:
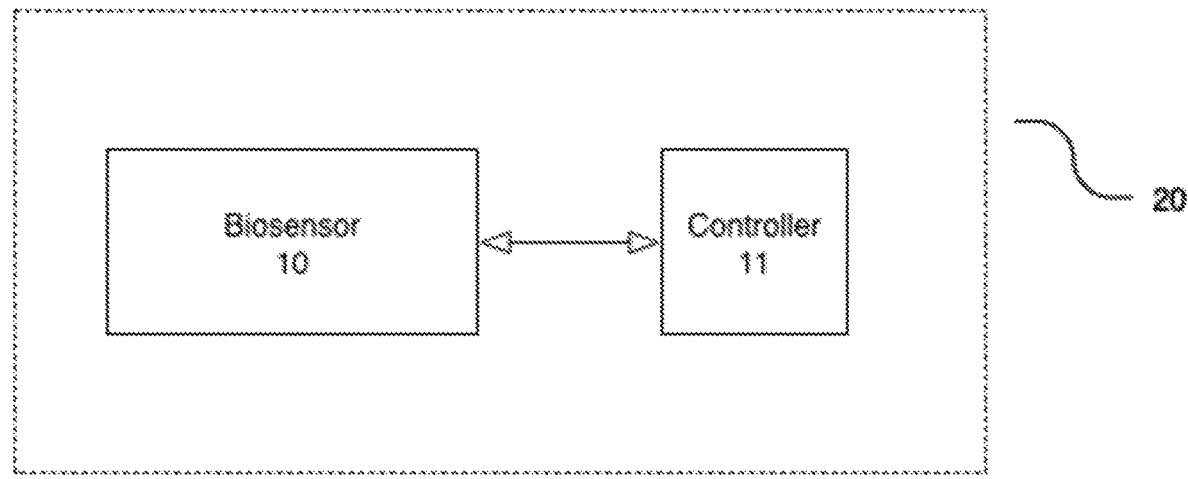
FIG. 3A illustrates a schematic of a biosensor in communication with a controller in accordance with one embodiment of the present disclosure.
Figure 3B:
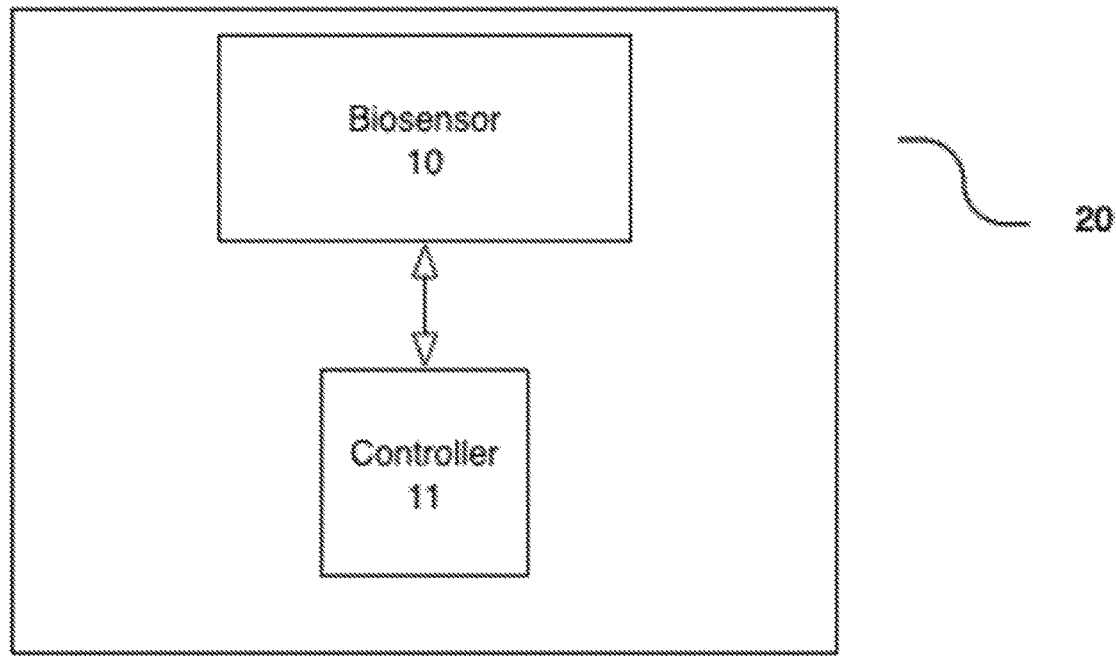
FIG. 3B illustrates a schematic of a sensor unit comprising a biosensor and a controller in accordance with one embodiment of the present disclosure.
Figure 3C:
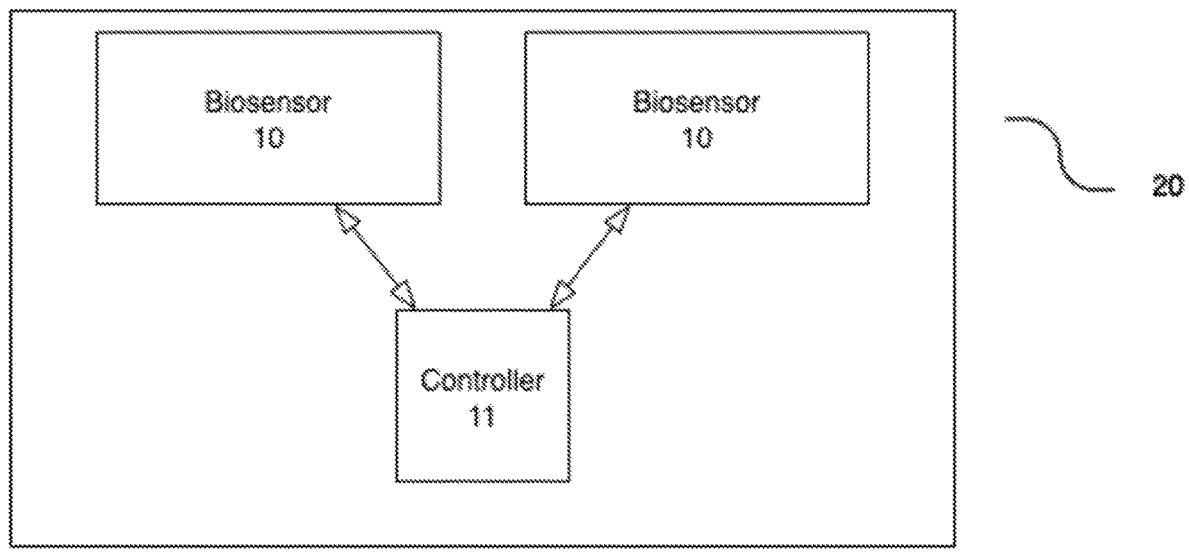
FIG. 3C illustrates a schematic of a sensor unit comprising a plurality of biosensors and a controller in accordance with one embodiment of the present disclosure.

In another aspect of the present disclosure is a sensor unit 20 incorporating one or more of the biosensors 10 of the present disclosure. As depicted in FIGS. 3A and 3B, the sensor unit 20 may be coupled to a controller 11 such that current changes due to the binding of ethylene to the ethylene receptor molecules may be measured and/or recorded. In some embodiments, the sensor unit 20 comprises a biosensor 10 and a controller 11, where the biosensor 10 and controller 11 are provided in separate housings (FIG. 3A). Alternatively, the sensor unit 20 comprises a biosensor 10 and a controller 11, where the biosensor 10 and controller 11 are coupled together, such as within the same housing or where both are provided on a chip. FIG. 3C illustrates a sensor unit 20 comprising at least two biosensors 10, each independently in communication with a controller 11. While FIG. 3C illustrates a sensor unit 20 comprising only two biosensors 10, the skilled artisan will appreciate that any number of biosensors 10 may be coupled to a single controller 11, e.g. 3, 4, 5, 10, or more biosensors.

Figure 3D:
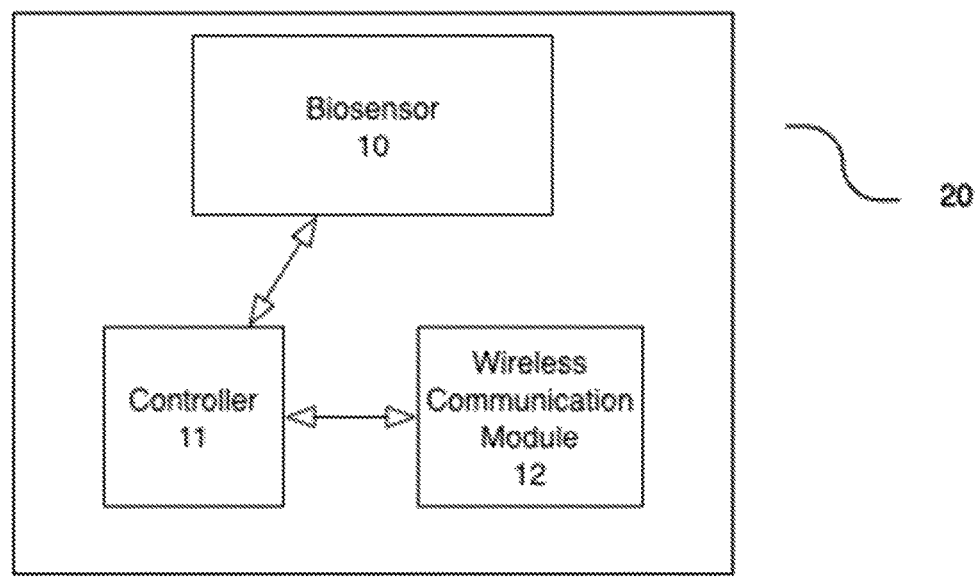
FIG. 3D illustrates a schematic of a sensor unit comprising a biosensor, a controller, and a wireless communications module in accordance with one embodiment of the present disclosure.
Figure 3E:
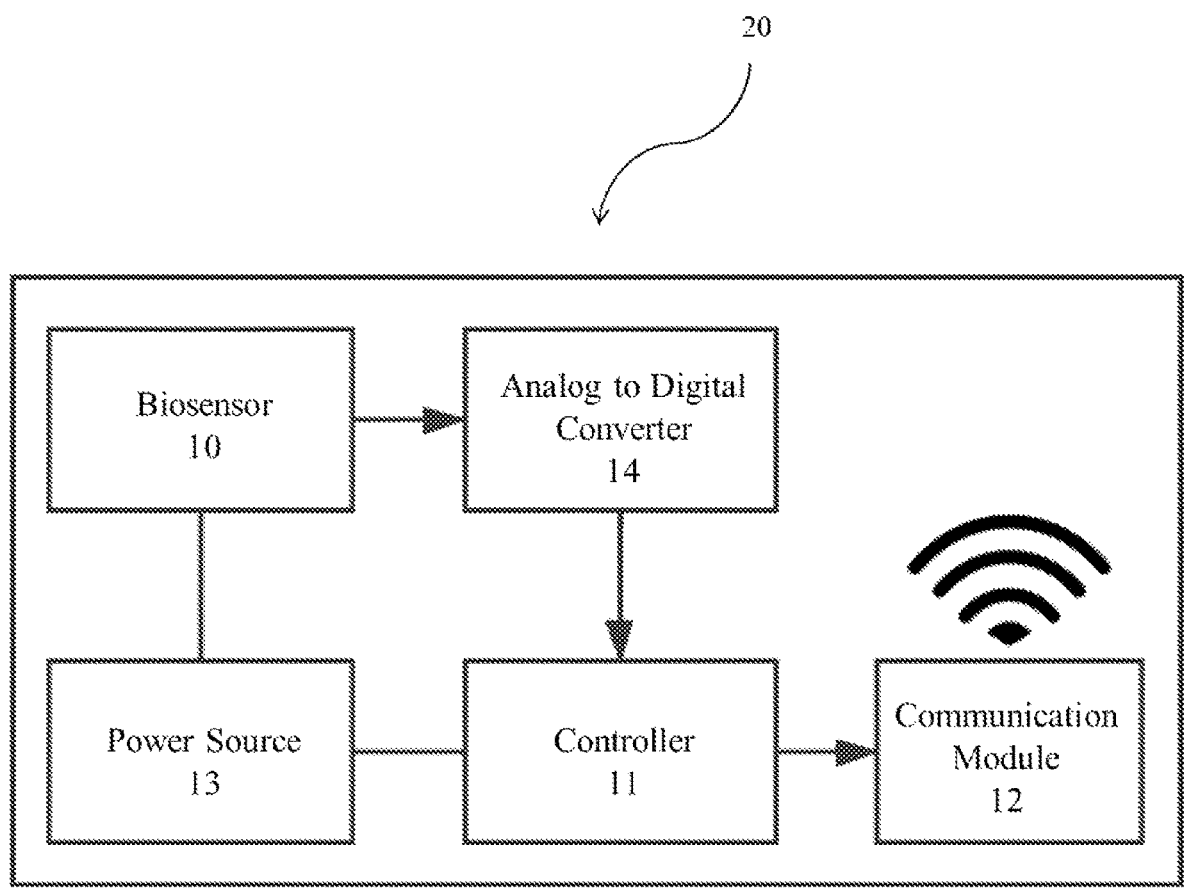
FIG. 3E illustrates a schematic of a sensor unit comprising a biosensor, a controller, a power source, an analog to digital converter, and a wireless communications module in accordance with one embodiment of the present disclosure.

In some embodiments, the controller includes a wireless communication module. In some embodiments, the wireless communications module is included within the controller 11 (i.e. within the same chip or module). In other embodiments, and with reference to FIG. 3D, the wireless communications module 12 is separate from controller 11. In some embodiments, and with reference to FIG. 3E, sensor unit 20 may comprise one or more biosensors 10; a power supply 13; a wireless communication module 12; and an analog to digital converter 14. In some embodiments, each sensor unit 20 may further comprise a memory module, e.g. volatile (e.g. RAM, etc.) and non-volatile (e.g. ROM, flash-memory, etc.) memory, additional processors or programmable circuits, other communication means (e.g. wired network communication), timers, oscillators, motion detectors, GPS modules, or any other helper device or circuit.

Figure 4:
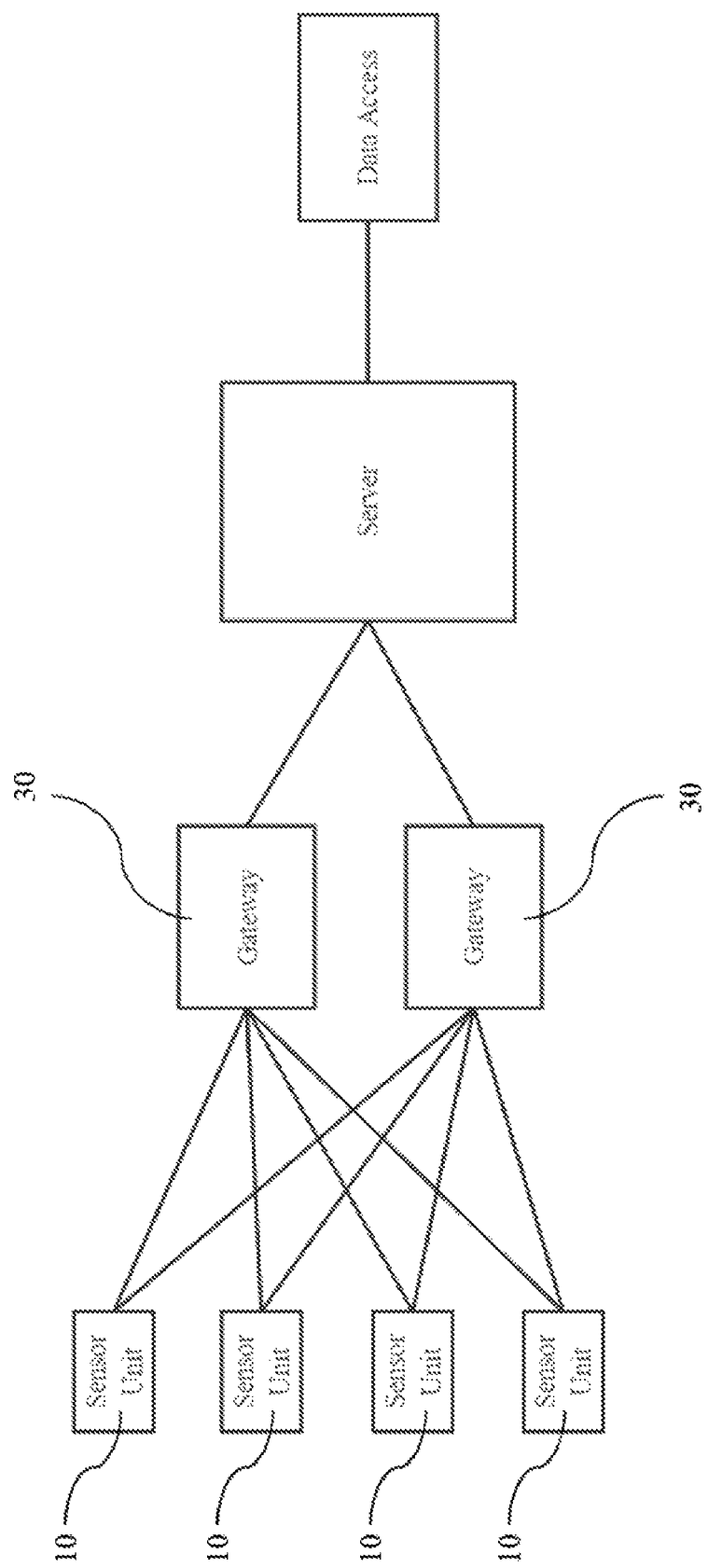
FIG. 4 illustrates a plurality of sensor units in wireless communication with a wireless gateway in accordance with one embodiment of the present disclosure.

In some embodiments, multiple sensor units 20 may be in wireless communication with each other or in wireless communication with a gateway 30, a server 31, storage device, etc. (see FIG. 4). In some embodiments, each sensor unit 20 may communicate via infrared pulses, radio waves, ultrasonic waves, or another wireless communication medium. In some embodiments, wireless communications are through a standard protocol, for example a Zigbee mesh network, LoRaWAN, 802.11 WiFi, or Bluetooth. Proprietary solutions could also be used. Wireless communication protocols will typically be accomplished using integrated circuits or modules specifically designed for the purpose. Modules appropriate for the purpose include those manufactured by, for example, Digi International, Synapse Wireless, Motorola, or Panasonic.

In some embodiments, the sensor units 20 have means for communicating with each other, with the wireless gateway, and/or with other network units, thus establishing a sensor network of any suitable kind. A network of the sensor units (a "sensor network") may be more or less organized, with none or any level of central control. In some embodiments, the wireless gateway may act as a common network controller for organizing the wireless sensors, e.g. by assigning IP-addresses in an IP network configuration. In some embodiments, the wireless gateway is a network unit that avails access in some sense between the individual sensor units of the sensor network and one or more external units. The wireless gateway may, for example, comprise a conventional wireless network gateway hardware for establishing access and routing between different networks, e.g. the wireless sensors with WiFi capabilities and the Internet or any other network, or e.g. a GSM or other cellular network communication unit. The wireless gateway may thus comprise one or more of the functionalities and tasks of conventional gateways, access points, routers, bridges, network address assigning or resolving, security controllers, web servers, etc. In some embodiments, the wireless gateway also carries out the task of collecting and possibly refining data and information from the individual sensor units of the sensor network.

In addition, the wireless gateway 30 may comprise a sensor unit 20 or it may be a sensor-free unit entirely dedicated to collecting data from all the sensor units 20. The wireless gateway 30 may further comprise positioning means for obtaining an initial position for itself, e.g. by means of a GPS unit which is feasible if located outside the biomass and heavy buildings or containers. The gateway 30 may also be provided with its position manually by the user, or it may simply be defining the center of the world as far as the sensor units 20 are concerned, i.e. the origin or other reference position in their positioning grid.

In some embodiments, the biosensor 10 is calibrated by exposing it to fixed concentrations of ethylene, and the voltage is measured. A linear correlation between voltage and ethylene concentration is established, and this standard can be used to measure ethylene concentrations outside of the tested range.

EXAMPLES

Receptor Isolation

Ethylene receptor genes expressed via plasmid, such as ETR1, ETR2, or ETR3, were transformed into bacteria. Following transformation, bacteria were streaked onto an agar plate, and after 12-24 hrs of incubation colonies form upon the surface. If using an antibacterial resistance plasmid, the agar should also contain the selected antibiotic. Colonies were picked and sequenced to ensure proper insertion of plasmidic DNA. Following the selection of properly expressing colonies, bacteria were amplified in LB broth for the desired yield. Typically, bacteria are grown in between 2 mL-1 L of broth for 12-18 hrs at 37 degrees Celsius.

Following bacterial growth, the bacteria were centrifuged, and the LB broth was removed. The bacterial pellet was treated with a protein extraction agent, and protein extraction was performed according to protocols specific to the reagent used. Specific protein isolation could be performed via centrifugation, if the protein is of known concentration, via antibody pulldown protocols, or by amending the plasmidic sequence to include a specific binding site, such as a poly-histidine tail, and using an affinity column to isolate the protein.

Biosensor Testing 1

Figure 5:
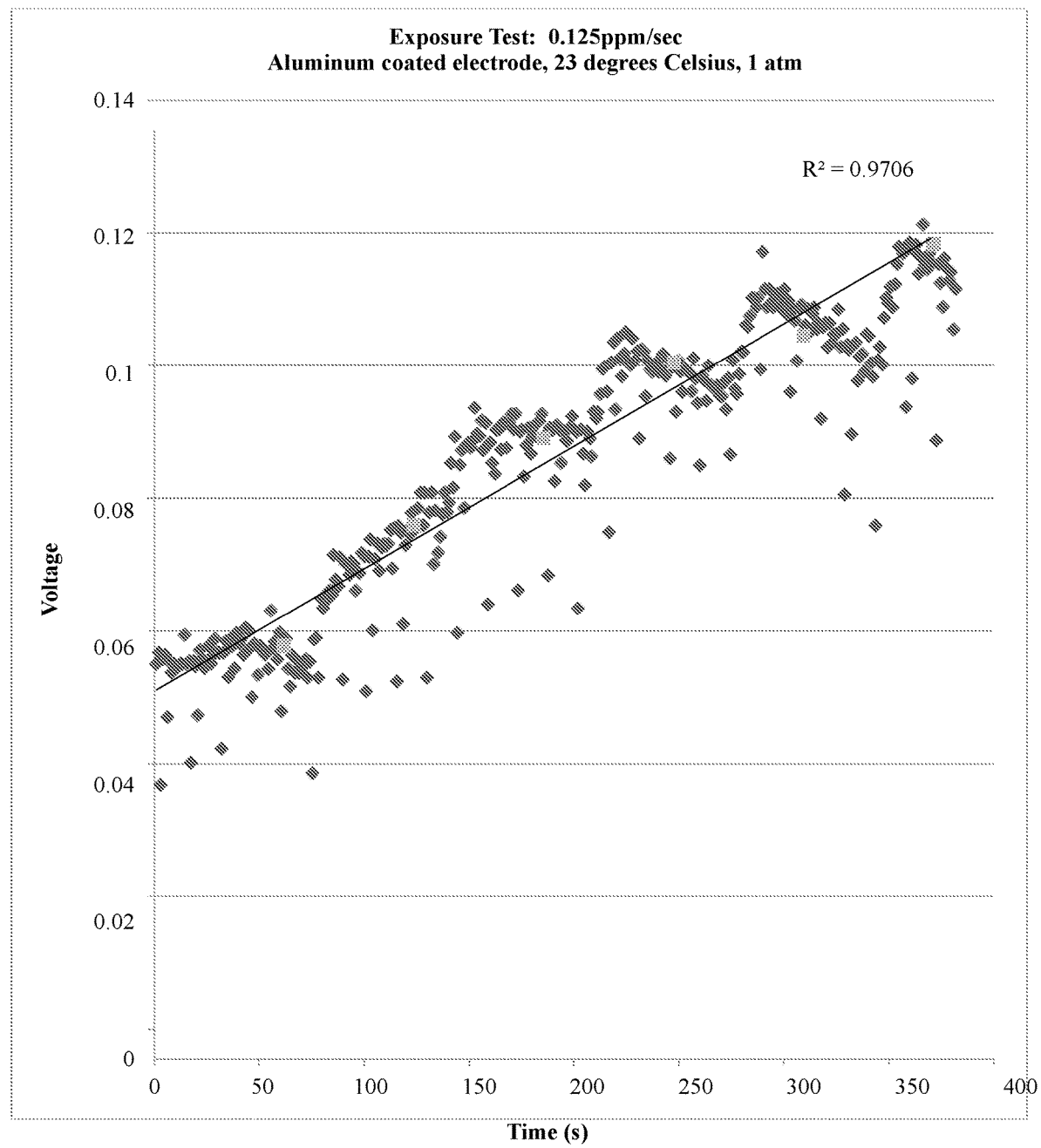
FIG. 5 provides a graph setting forth the results of an exposure test to about 7.5 ppm/min or ethylene. An ethylene biosensor was exposed to about 7.5 ppm/min of ethylene gas at standard atmospheric conditions within a confined about 5 L container. The voltage output correlated in a statistically significant manner to the overall ethylene concentration within the container.
Figure 6:
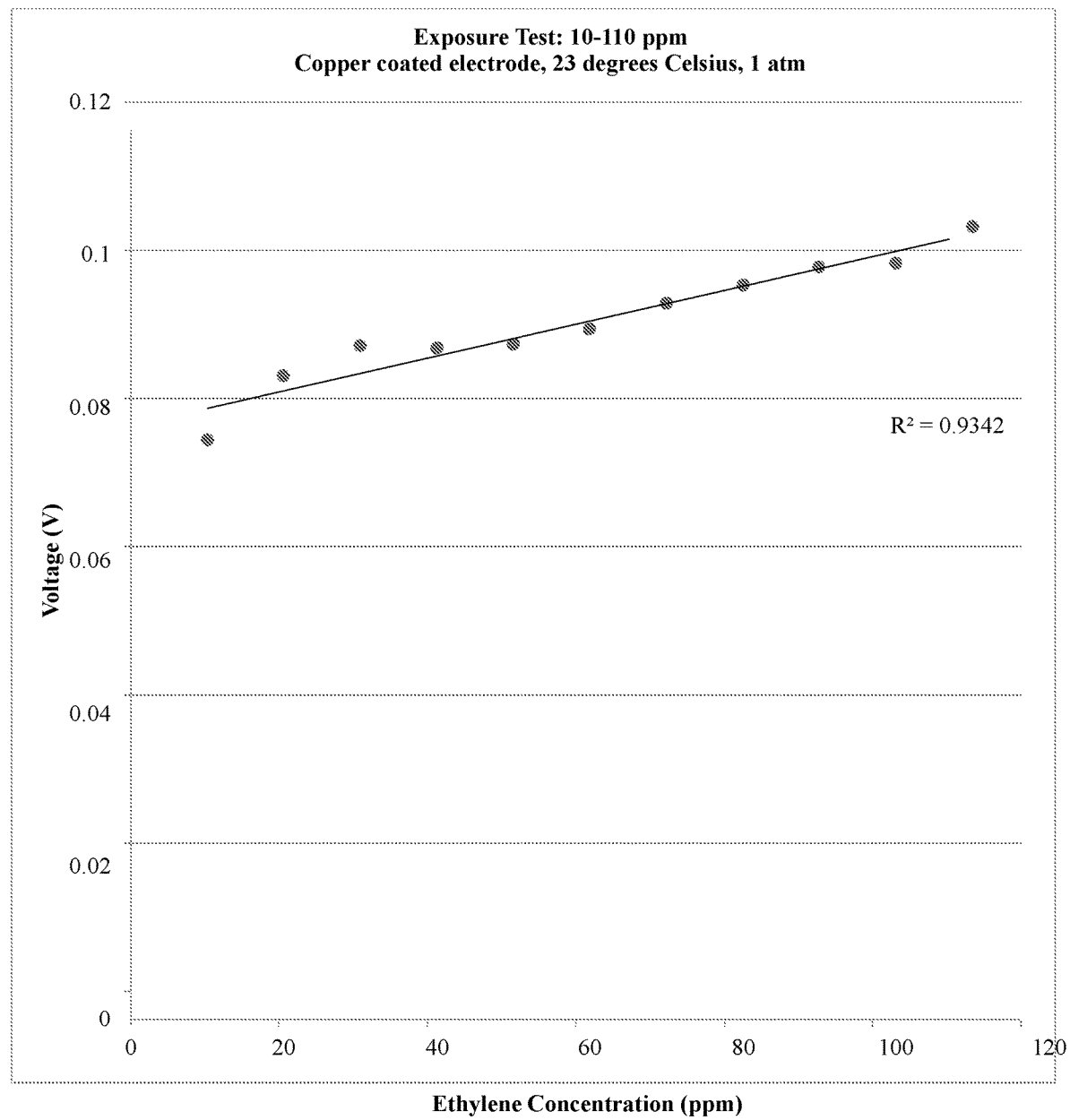
FIG. 6 provides a graph setting forth the results of an exposure test for about 10 to about 110 ppm of ethylene under standard atmospheric conditions. A biosensor was exposed from about 10 to about 110 ppm of ethylene. A reading was taken about at every 10 ppm.
Figure 7:
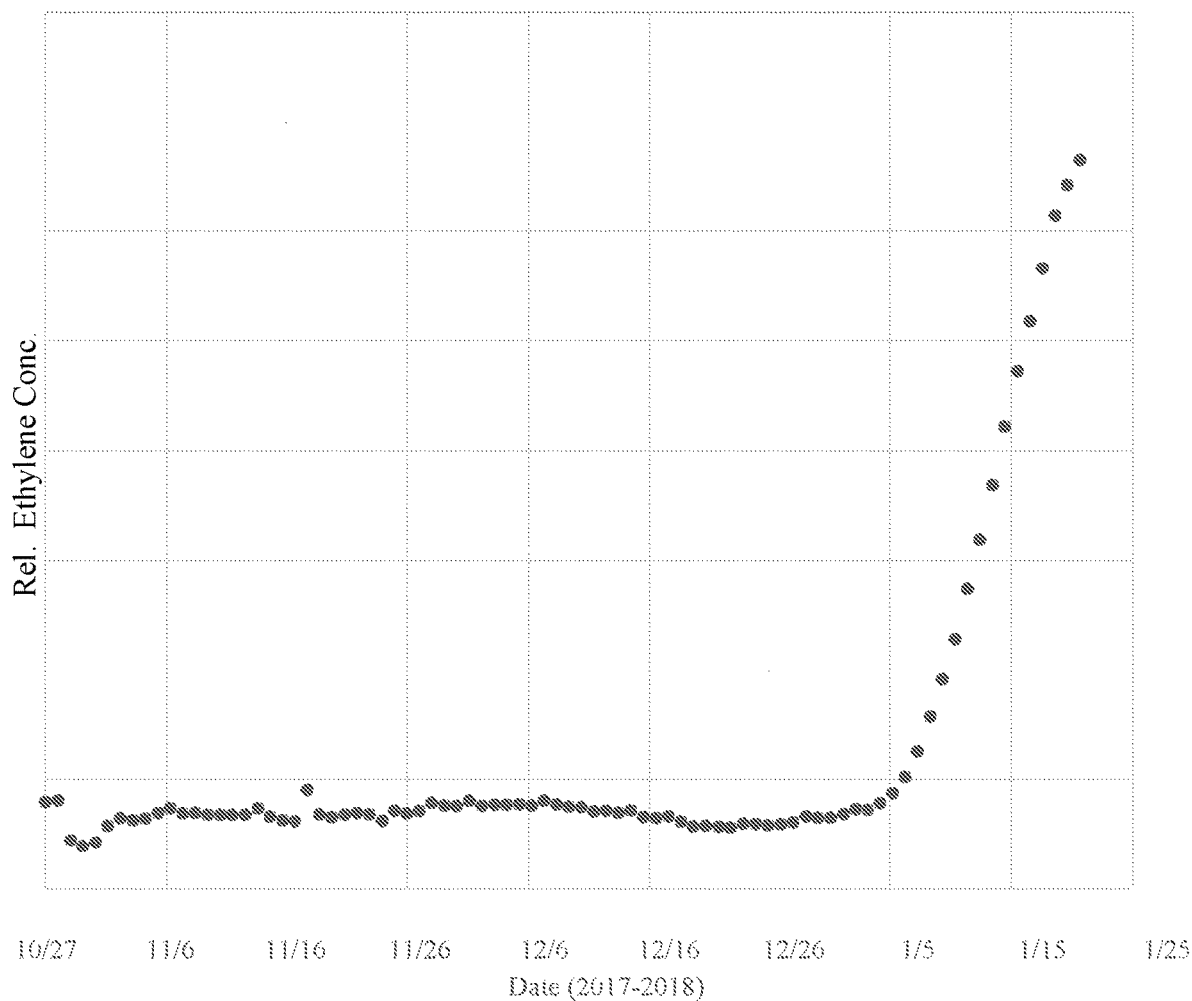
FIG. 7 provides a graph setting forth the results of ethylene testing using a biosensor of the present disclosure, where the ethylene concentration spike corresponds to quality control data, which indicated a change in fruit maturity.

An ethylene biosensor including the components described herein (about 200 uL of about 10% pyrrole mediator layer with about 0.015 mg/mm of *Arabidopsis* ETR1 upon an about 2 square inch copper electrode) was placed into a 5 L airtight vacuum chamber at standard atmospheric conditions. A biosensor consisting of an aluminum electrode, pyrrole mediator, and 100 ng of protein was exposed to ethylene at a concentration of about 0.125 ppm/sec for about 375 seconds. The voltage output of the sensor was measured continuously during ethylene exposure (see FIG. 5). Voltage outputs correlated linearly with linear exposure of ethylene to the biosensor, establishing a standard relationship between voltage and ethylene concentration. This correlation was statistically significant, with an R-squared value of about 0.97. The resulting equation generated by correlating ethylene exposure to voltage output, can be used to predict ethylene concentrations outside of the standard's bounds. This standard was replicated for a greater range of ethylene concentrations in FIG. 6, which analyzed the performance of a biosensor with a copper electrode, about 100 uL of pyrrole mediator, and about 100 uL of protein. This figure supported the linear relationship between voltage and ethylene concentration for a greater range of ethylene concentrations.

Biosensor Testing 2

The sensor (about 200 uL of an about 5% pyrrole mediator with about 0.015 mg/mm of *Arabidopsis* ETR1 upon a two square inch aluminum electrode) was tested within controlled atmosphere storage of apples. Depicts an experiment conducted for a period of 82 days within a controlled atmosphere storage room kept at 1 degree Celsius, about 2% $O_2$, and about 0.6% $CO_2$, with 2,000 bins of honey crisp apples. On day 70, the relative ethylene concentration within the controlled atmosphere storage room spiked, indicating the beginning of senescence for the fruit within the storage room (see FIG. 8). Using this data, a prediction was made for the room based on the senescence curve of honey crisp apples that the storage room had 1-2 months prior to experiencing significant maturity related losses due to fruit senescence. This data correlated with quality control data of fruit samples pulled from the room following its opening. This result indicates the predictive ability of an ethylene sensor in determining fruit senescence, which may be used to mitigate losses within the food supply chain.

Additional Embodiment 1: A biosensor comprising: (a) a reference electrode comprising (i) a mediator layer deposited on a base electrode; and (ii) a receptor layer deposited on the mediator layer, wherein the receptor layer comprises an ethylene receptor; (b) a working electrode in communication with the reference electrode; and (c) a counter electrode.

Additional Embodiment 2: The biosensor of additional embodiment 1, wherein the base electrode is comprised of a material selected from the group consisting of copper and silver.

Additional Embodiment 3: The biosensor of additional embodiment 1, wherein the base electrode comprises a coating of a material selected from the group consisting of copper and silver.

Additional Embodiment 4: The biosensor of additional embodiment 1, wherein the ethylene receptor comprises a nucleotide sequence having at least 90% sequence identity to a wild-type polynucleotide sequence of an ethylene receptor gene.

Additional Embodiment 5: The biosensor of additional embodiment 1, wherein the ethylene receptor is derived from *Zea mays* or *Arabidopsis*.

Additional Embodiment 6: The biosensor of additional embodiment 1, wherein the ethylene receptor comprises an amino acid sequence having at least 90% identity to that of SEQ ID NO: 1.

Additional Embodiment 7: The biosensor of additional embodiment 1, wherein the ethylene receptor comprises an amino acid sequence having at least 90% identity to that of SEQ ID NO: 2.

Additional Embodiment 8: The biosensor of additional embodiment 1, wherein the ethylene receptor comprises an amino acid sequence having at least 90% identity to that of SEQ ID NO: 3.

Additional Embodiment 9: The biosensor of additional embodiment 1, wherein the ethylene receptor comprises an amino acid sequence having at least 90% identity to that of SEQ ID NO: 4.

Additional Embodiment 10: The biosensor of additional embodiment 1, wherein the receptor layer comprises between about 10 to about 1000 nanograms of ethylene receptor.

Additional Embodiment 11: The biosensor of additional embodiment 1, wherein the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

Additional Embodiment 12: A stack comprising: (a) a mediator layer, and (b) a receptor layer in contact with the mediator layer, wherein the receptor layer comprises one or more ethylene receptor proteins.

Additional Embodiment 13: The stack of additional embodiment 12, wherein the one or more ethylene receptor proteins are selected from the group consisting of ETR1, ETR2, ETR3, and ETR4.

Additional Embodiment 14: The stack of additional embodiment 12, wherein the one or more ethylene receptor proteins comprises an amino acid sequence having at least 90% identity to any of SEQ ID NOS: 1-4.

Additional Embodiment 15: The stack of additional embodiment 12, wherein the receptor layer comprises between about 0.038 mg/mm to about 0.38 mg/mm nanograms of ethylene receptor proteins.

Additional Embodiment 16: The stack of additional embodiment 12, wherein the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

Additional Embodiment 17: A reference electrode comprising the stack of any one of additional embodiments 12 to 16 deposited on a base electrode.

Additional Embodiment 18: The reference electrode of additional embodiment 17, wherein the base electrode comprises a coating including copper or silver.

Additional Embodiment 19: A biosensor comprising the reference electrode of any one of additional embodiments 17-18; and a working electrode in communication with the reference electrode.

Additional Embodiment 20: A sensor unit comprising the biosensor of any one of additional embodiments 1 to 11 and 19; and a controller in communication with the biosensor.

Additional Embodiment 21: The sensor unit of additional embodiment 20, wherein the controller comprises a communication module.

Additional Embodiment 22: The sensor unit of additional embodiment 21, wherein the communication module is a wireless communication module.

Additional Embodiment 23: A system comprising a plurality of the sensor units of additional embodiment 22, wherein the plurality of sensor units are each independently in wireless communication with a receiver module, gateway, or storage module.

Additional Embodiment 24: A container comprising at least one of the sensor units of any one of additional embodiments 20 to 22.

Additional Embodiment 25: A biosensor comprising: (a) a reference electrode comprising (i) a mediator layer deposited on a base electrode; and (ii) a receptor layer deposited on the mediator layer, wherein the receptor layer comprises an ethylene receptor; and (b) a working electrode in communication with the reference electrode.

Additional Embodiment 26: The biosensor of additional embodiment 25, wherein the base electrode is comprised of a material selected from the group consisting of copper and silver.

Additional Embodiment 27: The biosensor of additional embodiment 25, wherein the base electrode comprises a coating of a material selected from the group consisting of copper and silver.

Additional Embodiment 28: The biosensor of additional embodiment 25, wherein the ethylene receptor comprises a nucleotide sequence having at least 90% sequence identity to a wild-type polynucleotide sequence of an ethylene receptor gene.

Additional Embodiment 29: The biosensor of additional embodiment 25, wherein the ethylene receptor is derived from *Zea mays* or *Arabidopsis*.

Additional Embodiment 30: The biosensor of additional embodiment 25, wherein the ethylene receptor comprises an amino acid sequence having at least 90% identity to that of SEQ ID NO: 1.

Additional Embodiment 31: The biosensor of additional embodiment 25, wherein the ethylene receptor comprises an amino acid sequence having at least 90% identity to that of SEQ ID NO: 2.

Additional Embodiment 32: The biosensor of additional embodiment 25, wherein the ethylene receptor comprises an amino acid sequence having at least 90% identity to that of SEQ ID NO: 3.

Additional Embodiment 33: The biosensor of additional embodiment 25, wherein the ethylene receptor comprises an amino acid sequence having at least 90% identity to that of SEQ ID NO: 4.

Additional Embodiment 34: The biosensor of additional embodiment 25, wherein the receptor layer comprises between about 10 to about 1000 nanograms of ethylene receptor.

Additional Embodiment 35: The biosensor of additional embodiment 25, wherein the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

Additional Embodiment 36: A stack comprising: (a) a mediator layer, and (b) a receptor layer in contact with the mediator layer, wherein the receptor layer comprises an ethylene receptor protein.

Additional Embodiment 37: The stack of additional embodiment 36, wherein the ethylene receptor protein is selected from the group consisting of ETR1, ETR2, ETR3, and ETR4.

Additional Embodiment 38: The stack of additional embodiment 36, wherein the ethylene receptor protein comprises an amino acid sequence having at least 90% identity to any of SEQ ID NOS: 1-4.

Additional Embodiment 39: The stack of additional embodiment 36, wherein the receptor layer comprises between about 0.038 mg/mm to about 0.38 mg/mm nanograms of ethylene receptor proteins.

Additional Embodiment 40: The stack of additional embodiment 36, wherein the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

Additional Embodiment 41: A reference electrode comprising the stack of any one of additional embodiments 12 to 16 deposited on a base electrode.

Additional Embodiment 42: The reference electrode of additional embodiment 41, wherein the base electrode comprises a coating including copper or silver.

Additional Embodiment 43: A biosensor comprising the reference electrode of any one of additional embodiments 17-18; and a working electrode in communication with the reference electrode.

Additional Embodiment 44: A sensor unit comprising the biosensor of any one of additional embodiments 1 to 11 and 19; and a controller in communication with the biosensor.

Additional Embodiment 45: The sensor unit of additional embodiment 44, wherein the controller comprises a communication module.

Additional Embodiment 46: The sensor unit of additional embodiment 45, wherein the communication module is a wireless communication module.

Additional Embodiment 47: A system comprising a plurality of the sensor units of additional embodiment 22, wherein the plurality of sensor units are each independently in wireless communication with a receiver module, gateway, or storage module.

Additional Embodiment 48: A container comprising at least one of the sensor units of any one of additional embodiments 44 to 46.

The invention claimed is:

1. A two-electrode biosensor comprising (a) a reference electrode, and (b) a working electrode in communication with the reference electrode; wherein the reference electrode comprises (i) a mediator layer in communication with a base electrode; and (ii) a receptor layer in communication with the mediator layer, wherein the receptor layer comprises one or more ethylene receptor proteins.

2. The two-electrode biosensor of claim 1, wherein the one or more ethylene receptor proteins are naturally occurring.

3. The two-electrode biosensor of claim 2, wherein the naturally occurring ethylene receptor proteins comprises a nucleotide sequence having at least 90% identity to a wild-type polynucleotide sequence of an ethylene receptor gene.

4. The two-electrode biosensor of claim 1, wherein the one or more ethylene receptor proteins are synthetic.

5. The two-electrode biosensor of claim 1, wherein the one or more ethylene receptor proteins are selected from the group consisting of ETR1, ETR2, ETR3, and ETR4.

6. The two-electrode biosensor of claim 1, wherein the one or more ethylene receptor proteins is ETR1.

7. The two-electrode biosensor of claim 1, wherein the one or more ethylene receptor proteins are selected from the group consisting of ZmERS1, ZmETR2, ZmETR2 variants, ZmETR9 and ZmETR40.

8. The two-electrode biosensor of claim 1, wherein the one or more ethylene receptor proteins are derived from one of Lactuca Sativa, Bryophyta, Petunia, and Solanum lycopersicum.

9. The two-electrode biosensor of claim 1, wherein the one or more ethylene receptor proteins have an amino acid sequence having at least 80% identity to any one of SEQ ID NOS: 1-4.

10. The two-electrode biosensor of claim 1, wherein the one or more ethylene receptor proteins have an amino acid sequence having at least 85% identity to any one of SEQ ID NOS: 1-4.

11. The two-electrode biosensor of claim 1, wherein the one or more ethylene receptor proteins have an amino acid sequence having at least 90% identity to any one of SEQ ID NOS: 1-4.

12. The two-electrode biosensor of claim 1, wherein the one or more ethylene receptor proteins have an amino acid sequence having at least 95% identity to any one of SEQ ID NOS: 1-4.

13. The two-electrode biosensor of claim 1, wherein the one or more ethylene receptor proteins have an amino acid sequence having at least 99% identity to any one of SEQ ID NOS: 1-4.

14. The two-electrode biosensor of claim 1, wherein the mediator layer comprises at least one of potassium ferricyanide, methyl viologen, ferrocene, cysteamine, mercaptopropionic acid, mercaptobenzoic acid, mercaptoundecanoic acid, ruthenium chloride, naphthol green, or polypyrrole.

15. The two-electrode biosensor of claim 1, wherein the base electrode is comprised of a material selected from the group consisting of copper and silver.

16. The two-electrode biosensor of claim 1, wherein the base electrode comprises a coating comprising a material selected from the group consisting of copper and silver.

17. The two-electrode biosensor of claim 1, wherein the mediator layer comprises $FeCl_3$.

18. The two-electrode biosensor of claim 1, wherein the working electrode comprises one or more pores or punctures having a radius ranging from between about 2 angstroms to about 2 mm.

19. The two-electrode biosensor of claim 1, wherein the receptor layer comprises between about 0.038 mg/mm to about 0.38 mg/mm of ethylene receptor proteins.

20. A sensor unit comprising the biosensor of claim 1 and a controller in communication with the biosensor.

21. A biosensor consisting essentially of (a) a reference electrode, and (b) a working electrode in communication with the reference electrode; wherein the reference electrode comprises (i) a mediator layer in communication with a base electrode; and (ii) a receptor layer in communication with the mediator layer, wherein the receptor layer comprises one or more ethylene receptor proteins.

22. The biosensor of claim 21, wherein the receptor layer comprises between about 0.038 mg/mm to about 0.38 mg/mm of ethylene receptor proteins.

23. The biosensor of claim 21, wherein the receptor layer comprises between about 0.038 mg/mm to about 0.38 mg/mm of ethylene receptor proteins.

24. A sensor unit comprising the biosensor of claim 21 and a controller in communication with the biosensor.

25. A biosensor consisting of (a) a reference electrode comprising (i) a mediator layer in communication with a base electrode; and (ii) a receptor layer in communication with the mediator layer, wherein the receptor layer comprises one or more ethylene receptor proteins; and (b) a working electrode in communication with the reference electrode.

* * * * *

SEQUENCE LISTING

<160> NUMBER OF SEQ ID NOS: 4

<210> SEQ ID NO 1
<211> LENGTH: 738
<212> TYPE: PRT
<213> ORGANISM: Arabidopsis thaliana
<220> FEATURE:
<221> NAME/KEY: misc_feature
<223> OTHER INFORMATION: ETHYLENE RECEPTOR 1 (ETR1)

<400> SEQUENCE: 1

```
Met Glu Val Cys Asn Cys Ile Glu Pro Gln Trp Pro Ala Asp Glu Leu
1               5                   10                  15

Leu Met Lys Tyr Gln Tyr Ile Ser Asp Phe Phe Ile Ala Ile Ala Tyr
            20                  25                  30

Phe Ser Ile Pro Leu Glu Leu Ile Tyr Phe Val Lys Lys Ser Ala Val
        35                  40                  45

Phe Pro Tyr Arg Trp Val Leu Val Gln Phe Gly Ala Phe Ile Val Leu
    50                  55                  60

Cys Gly Ala Thr His Leu Ile Asn Leu Trp Thr Phe Thr Thr His Ser
65                  70                  75                  80

Arg Thr Val Ala Leu Val Met Thr Thr Ala Lys Val Leu Thr Ala Val
                85                  90                  95

Val Ser Cys Ala Thr Ala Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
    130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
    210                 215                 220

Lys Ile Ser Pro Asn Ser Pro Val Ala Arg Leu Arg Pro Val Ser Gly
225                 230                 235                 240

Lys Tyr Met Leu Gly Glu Val Val Ala Val Arg Val Pro Leu Leu His
                245                 250                 255

Leu Ser Asn Phe Gln Ile Asn Asp Trp Pro Glu Leu Ser Thr Lys Arg
            260                 265                 270

Tyr Ala Leu Met Val Leu Met Leu Pro Ser Asp Ser Ala Arg Gln Trp
        275                 280                 285

His Val His Glu Leu Glu Leu Val Glu Val Val Ala Asp Gln Val Ala
    290                 295                 300

Val Ala Leu Ser His Ala Ala Ile Leu Glu Glu Ser Met Arg Ala Arg
305                 310                 315                 320

Asp Leu Leu Met Glu Gln Asn Val Ala Leu Asp Leu Ala Arg Arg Glu
                325                 330                 335

Ala Glu Thr Ala Ile Arg Ala Arg Asn Asp Phe Leu Ala Val Met Asn
            340                 345                 350
```

His Glu Met Arg Thr Pro Met His Ala Ile Ile Ala Leu Ser Ser Leu
            355                 360                 365
Leu Gln Glu Thr Glu Leu Thr Pro Glu Gln Arg Leu Met Val Glu Thr
        370                 375                 380
Ile Leu Lys Ser Ser Asn Leu Leu Ala Thr Leu Met Asn Asp Val Leu
385                 390                 395                 400
Asp Leu Ser Arg Leu Glu Asp Gly Ser Leu Gln Leu Glu Leu Gly Thr
                405                 410                 415
Phe Asn Leu His Thr Leu Phe Arg Glu Val Leu Asn Leu Ile Lys Pro
            420                 425                 430
Ile Ala Val Val Lys Lys Leu Pro Ile Thr Leu Asn Leu Ala Pro Asp
        435                 440                 445
Leu Pro Glu Phe Val Val Gly Asp Glu Lys Arg Leu Met Gln Ile Ile
    450                 455                 460
Leu Asn Ile Val Gly Asn Ala Val Lys Phe Ser Lys Gln Gly Ser Ile
465                 470                 475                 480
Ser Val Thr Ala Leu Val Thr Lys Ser Asp Thr Arg Ala Ala Asp Phe
                485                 490                 495
Phe Val Val Pro Thr Gly Ser His Phe Tyr Leu Arg Val Lys Val Lys
            500                 505                 510
Asp Ser Gly Ala Gly Ile Asn Pro Gln Asp Ile Pro Lys Ile Phe Thr
        515                 520                 525
Lys Phe Ala Gln Thr Gln Ser Leu Ala Thr Arg Ser Ser Gly Gly Ser
    530                 535                 540
Gly Leu Gly Leu Ala Ile Ser Lys Arg Phe Val Asn Leu Met Glu Gly
545                 550                 555                 560
Asn Ile Trp Ile Glu Ser Asp Gly Leu Gly Lys Gly Cys Thr Ala Ile
                565                 570                 575
Phe Asp Val Lys Leu Gly Ile Ser Glu Arg Ser Asn Glu Ser Lys Gln
            580                 585                 590
Ser Gly Ile Pro Lys Val Pro Ala Ile Pro Arg His Ser Asn Phe Thr
        595                 600                 605
Gly Leu Lys Val Leu Val Met Asp Glu Asn Gly Val Ser Arg Met Val
    610                 615                 620
Thr Lys Gly Leu Leu Val His Leu Gly Cys Glu Val Thr Thr Val Ser
625                 630                 635                 640
Ser Asn Glu Glu Cys Leu Arg Val Val Ser His Glu His Lys Val Val
                645                 650                 655
Phe Met Asp Val Cys Met Pro Gly Val Glu Asn Tyr Gln Ile Ala Leu
            660                 665                 670
Arg Ile His Glu Lys Phe Thr Lys Gln Arg His Gln Arg Pro Leu Leu
        675                 680                 685
Val Ala Leu Ser Gly Asn Thr Asp Lys Ser Thr Lys Glu Lys Cys Met
    690                 695                 700
Ser Phe Gly Leu Asp Gly Val Leu Leu Lys Pro Val Ser Leu Asp Asn
705                 710                 715                 720
Ile Arg Asp Val Leu Ser Asp Leu Leu Glu Pro Arg Val Leu Tyr Glu
                725                 730                 735
Gly Met

<210> SEQ ID NO 2
<211> LENGTH: 773
<212> TYPE: PRT
<213> ORGANISM: Arabidopsis thaliana

```
<220> FEATURE:
<221> NAME/KEY: misc_feature
<223> OTHER INFORMATION: ETHYLENE RECEPTOR 2 (ETR2)

<400> SEQUENCE: 2

Met Val Lys Glu Ile Ala Ser Trp Leu Leu Ile Leu Ser Met Val Val
1               5                   10                  15

Phe Val Ser Pro Val Leu Ala Ile Asn Gly Gly Tyr Pro Arg Cys
            20                  25                  30

Asn Cys Glu Asp Glu Gly Asn Ser Phe Trp Ser Thr Glu Asn Ile Leu
            35                  40                  45

Glu Thr Gln Arg Val Ser Asp Phe Leu Ile Ala Val Ala Tyr Phe Ser
        50                  55                  60

Ile Pro Ile Glu Leu Leu Tyr Phe Val Ser Cys Ser Asn Val Pro Phe
65                  70                  75                  80

Lys Trp Val Leu Phe Glu Phe Ile Ala Phe Ile Val Leu Cys Gly Met
                85                  90                  95

Thr His Leu Leu His Gly Trp Thr Tyr Ser Ala His Pro Phe Arg Leu
            100                 105                 110

Met Met Ala Phe Thr Val Phe Lys Met Leu Thr Ala Leu Val Ser Cys
        115                 120                 125

Ala Thr Ala Ile Thr Leu Ile Thr Leu Ile Pro Leu Leu Leu Lys Val
    130                 135                 140

Lys Val Arg Glu Phe Met Leu Lys Lys Ala His Glu Leu Gly Arg
145                 150                 155                 160

Glu Val Gly Leu Ile Leu Ile Lys Lys Glu Thr Gly Phe His Val Arg
                165                 170                 175

Met Leu Thr Gln Glu Ile Arg Lys Ser Leu Asp Arg His Thr Ile Leu
            180                 185                 190

Tyr Thr Thr Leu Val Glu Leu Ser Lys Thr Leu Gly Leu Gln Asn Cys
        195                 200                 205

Ala Val Trp Met Pro Asn Asp Gly Gly Thr Glu Met Asp Leu Thr His
    210                 215                 220

Glu Leu Arg Gly Arg Gly Gly Tyr Gly Gly Cys Ser Val Ser Met Glu
225                 230                 235                 240

Asp Leu Asp Val Val Arg Ile Arg Glu Ser Asp Glu Val Asn Val Leu
                245                 250                 255

Ser Val Asp Ser Ser Ile Ala Arg Ala Ser Gly Gly Gly Asp Val
            260                 265                 270

Ser Glu Ile Gly Ala Val Ala Ala Ile Arg Met Pro Met Leu Arg Val
        275                 280                 285

Ser Asp Phe Asn Gly Glu Leu Ser Tyr Ala Ile Leu Val Cys Val Leu
    290                 295                 300

Pro Gly Gly Thr Pro Arg Asp Trp Thr Tyr Gln Glu Ile Glu Ile Val
305                 310                 315                 320

Lys Val Val Ala Asp Gln Val Thr Val Ala Leu Asp His Ala Ala Val
                325                 330                 335

Leu Glu Glu Ser Gln Leu Met Arg Glu Lys Leu Ala Glu Gln Asn Arg
            340                 345                 350

Ala Leu Gln Met Ala Lys Arg Asp Ala Leu Arg Ala Ser Gln Ala Arg
        355                 360                 365

Asn Ala Phe Gln Lys Thr Met Ser Glu Gly Met Arg Arg Pro Met His
    370                 375                 380

Ser Ile Leu Gly Leu Leu Ser Met Ile Gln Asp Glu Lys Leu Ser Asp
```

```
            385                 390                 395                 400
        Glu Gln Lys Met Ile Val Asp Thr Met Val Lys Thr Gly Asn Val Met
                        405                 410                 415

Ser Asn Leu Val Gly Asp Ser Met Asp Val Pro Asp Gly Arg Phe Gly
                        420                 425                 430

Thr Glu Met Lys Pro Phe Ser Leu His Arg Thr Ile His Glu Ala Ala
                        435                 440                 445

Cys Met Ala Arg Cys Leu Cys Leu Cys Asn Gly Ile Arg Phe Leu Val
                        450                 455                 460

Asp Ala Glu Lys Ser Leu Pro Asp Asn Val Val Gly Asp Glu Arg Arg
        465                 470                 475                 480

Val Phe Gln Val Ile Leu His Ile Val Gly Ser Leu Val Lys Pro Arg
                        485                 490                 495

Lys Arg Gln Glu Gly Ser Ser Leu Met Phe Lys Val Leu Lys Glu Arg
                        500                 505                 510

Gly Ser Leu Asp Arg Ser Asp His Arg Trp Ala Ala Trp Arg Ser Pro
                        515                 520                 525

Ala Ser Ser Ala Asp Gly Asp Val Tyr Ile Arg Phe Glu Met Asn Val
                        530                 535                 540

Glu Asn Asp Asp Ser Ser Ser Gln Ser Phe Ala Ser Val Ser Ser Arg
        545                 550                 555                 560

Asp Gln Glu Val Gly Asp Val Arg Phe Ser Gly Gly Tyr Gly Leu Gly
                        565                 570                 575

Gln Asp Leu Ser Phe Gly Val Cys Lys Lys Val Val Gln Leu Ile His
                        580                 585                 590

Gly Asn Ile Ser Val Val Pro Gly Ser Asp Gly Ser Pro Glu Thr Met
                        595                 600                 605

Ser Leu Leu Leu Arg Phe Arg Arg Pro Ser Ile Ser Val His Gly
                        610                 615                 620

Ser Ser Glu Ser Pro Ala Pro Asp His His Ala His Pro His Ser Asn
        625                 630                 635                 640

Ser Leu Leu Arg Gly Leu Gln Val Leu Leu Val Asp Thr Asn Asp Ser
                        645                 650                 655

Asn Arg Ala Val Thr Arg Lys Leu Leu Glu Lys Leu Gly Cys Asp Val
                        660                 665                 670

Thr Ala Val Ser Ser Gly Phe Asp Cys Leu Thr Ala Ile Ala Pro Gly
                        675                 680                 685

Ser Ser Ser Pro Ser Thr Ser Phe Gln Val Val Leu Asp Leu Gln
                        690                 695                 700

Met Ala Glu Met Asp Gly Tyr Glu Val Ala Met Arg Ile Arg Ser Arg
        705                 710                 715                 720

Ser Trp Pro Leu Ile Val Ala Thr Thr Val Ser Leu Asp Glu Met
                        725                 730                 735

Trp Asp Lys Cys Ala Gln Ile Gly Ile Asn Gly Val Val Arg Lys Pro
                        740                 745                 750

Val Val Leu Arg Ala Met Glu Ser Glu Leu Arg Arg Val Leu Leu Gln
                        755                 760                 765

Ala Asp Gln Leu Leu
                770

<210> SEQ ID NO 3
<211> LENGTH: 836
<212> TYPE: PRT
<213> ORGANISM: Oryza sativa
```

<220> FEATURE:
<221> NAME/KEY: misc_feature
<223> OTHER INFORMATION: ETHYLENE RECEPTOR 3 (ETR3) of Oryza sativa
      indica (RICE)

<400> SEQUENCE: 3

```
Met Leu Leu Ser Thr Trp Thr Pro Gly Cys Phe Gln Gly Asn Lys Ile
1               5                   10                  15

Leu Leu Arg Ser Leu Ile Thr Trp Tyr Tyr Leu Glu Phe Met Pro Lys
            20                  25                  30

Leu Arg Pro Phe Tyr Phe Leu Phe Tyr Leu Thr Leu Pro Ser Cys Ala
        35                  40                  45

Thr Asp Ser Pro Pro Ile Ser Asp Lys Ser Ser Ile Phe Leu Pro
    50                  55                  60

Leu Ala Gln Gln Gln Gln Leu Val His Trp Met Met Pro Pro Arg Phe
65                  70                  75                  80

Arg Cys Gln Asp Tyr Leu Leu Pro Leu Leu Leu Ala Leu Ser Pro Ala
                85                  90                  95

Ala Ala Ala Ala Arg Glu Val Glu Tyr His His Cys His Cys Asp Gly
            100                 105                 110

Gly Gly Gly Gly Gly Gly Gly Leu Trp Ser Met Asp Ser Ile Phe
        115                 120                 125

Arg Arg Gln Lys Val Ser Asp Leu Leu Ile Ala Ala Ala Tyr Phe Ser
130                 135                 140

Ile Pro Leu Glu Ile Leu Tyr Phe Val Ala Gly Leu Arg His Leu Leu
145                 150                 155                 160

Pro Phe Arg Trp Val Leu Val Gln Phe Gly Ala Phe Ile Val Leu Cys
                165                 170                 175

Gly Leu Thr His Leu Leu Thr Ala Phe Thr Tyr Glu Pro His Pro Phe
            180                 185                 190

Met Val Val Leu Leu Leu Thr Thr Ala Lys Phe Leu Thr Ala Leu Val
        195                 200                 205

Ser Phe Leu Thr Ala Ile Thr Leu Leu Thr Leu Ile Pro Gln Leu Leu
210                 215                 220

Arg Val Lys Val Arg Glu Ser Leu Leu Trp Leu Lys Ala Arg Glu Leu
225                 230                 235                 240

Asp Arg Glu Val Val Leu Met Lys Arg Gln Glu Glu Ala Ser Trp His
                245                 250                 255

Val Arg Met Leu Thr His Glu Ile Arg Lys Ser Leu Asp Arg His Thr
            260                 265                 270

Val Leu Tyr Thr Thr Leu Ile Glu Leu Ser Leu Val Leu Gly Leu Thr
        275                 280                 285

Asn Cys Ala Val Trp Met Pro Ala Ala Gly Glu Met Cys Leu Thr His
290                 295                 300

Glu Leu Arg Arg Asp Gly Gly Glu Asp Gly Val Val Gly Val Asp
305                 310                 315                 320

Asp Ala Asp Val Val Glu Val Arg Gly Ser Asp Gly Val Lys Leu Leu
                325                 330                 335

Gly Pro Asp Ser Val Leu Ala Ala Ser Gly Gly Lys Glu Glu Gly
            340                 345                 350

Thr Gly Ala Val Ala Ala Ile Arg Met Pro Met Leu Lys Val Ser Asp
        355                 360                 365

Phe Lys Gly Gly Thr Pro Glu Val Ile Gln Thr Ser Tyr Ala Val Leu
    370                 375                 380
```

```
Val Leu Val Pro Pro Ala Gly Lys Ser Trp Gly Arg His Glu Met Glu
385                 390                 395                 400

Ile Val Glu Val Val Ala Gly Gln Val Ala Val Ala Leu Ser His Ala
            405                 410                 415

Thr Leu Leu Glu Glu Ser Arg Ala Met Arg Asp Arg Leu Ala Glu Gln
            420                 425                 430

Asn Arg Glu Leu Leu Gln Ala Arg Arg Asp Ala Leu Met Ala Asn Glu
            435                 440                 445

Ala Arg Gln Ala Phe Gln Gly Val Met Ser Gln Gly Met Arg Arg Pro
450                 455                 460

Ile His Ser Ile Leu Gly Leu Val Ser Met Val Gln Glu Ala Leu
465                 470                 475                 480

Ala Pro Glu Gln Arg Leu Val Val Asp Thr Met Ala Arg Thr Ala Thr
            485                 490                 495

Val Val Ser Thr Leu Val Asn Asp Val Met Glu Met Ser Ala Asp Ser
            500                 505                 510

Arg Glu Arg Phe Pro Leu Glu Thr Arg Pro Phe His Leu His Ala Met
            515                 520                 525

Ile Arg Asp Ala Ala Cys Val Ala Arg Cys Leu Cys Asp Phe Arg Gly
530                 535                 540

Phe Gly Phe Ala Val His Val Glu Asn Ala Leu Pro Asp Leu Val Val
545                 550                 555                 560

Gly Asp Glu Arg Arg Ile Phe His Val Leu His Met Val Gly Asn
            565                 570                 575

Leu Ile Gly Arg Thr Glu Pro Gly His Val Thr Leu Arg Val Arg Ala
            580                 585                 590

Ala Asp Asp Asp Val Leu Asp Asp Arg Leu Gly Gln Arg Trp Asp Pro
595                 600                 605

Arg Trp Pro Ser Tyr Ser Thr Gly Tyr Ser Ser Val Lys Phe Val Ile
            610                 615                 620

Gly Val Lys Arg Gln Gln Asn Gly Asp Ala Gly Ser Pro Leu Ser Arg
625                 630                 635                 640

Arg Pro Ser Gly Lys Gly Ile Asp Leu Arg Leu Ser Phe Ser Met Cys
            645                 650                 655

Arg Lys Leu Val Gln Met Met Gln Gly Asn Ile Trp Ala Ile Asn Asp
            660                 665                 670

Pro Gln Gly Leu Pro Glu Ser Met Thr Leu Val Leu Arg Phe Gln Leu
            675                 680                 685

Gln Ser Pro Leu Thr Ser Ser Leu Gly Gly Ser Phe Glu Gln Lys
            690                 695                 700

His Ser Ser Pro Ser Cys Gln Ile Ala Gly Leu Lys Val Leu Leu Ile
705                 710                 715                 720

Asp Asp Asp Asp Asp Ile Asn Leu Val Val Ala Arg Lys Leu Leu Glu
            725                 730                 735

Lys Leu Gly Cys Val Val Ser Ser Pro Ser Gly Ser Gly Phe Leu
            740                 745                 750

Ser Ser Val Gly Ser Ser Ala Ala Ala Phe Gln Leu Val Met Val Asn
            755                 760                 765

Leu Glu Met Lys Arg Val Lys Ala Leu Asp Val Ala Thr Arg Ile Ser
            770                 775                 780

Gln Tyr Arg Ser Gly Arg Trp Pro Ile Val Met Ala Met Ala Ser Asp
785                 790                 795                 800

Gln Lys Ala Trp Glu Lys Cys Ala Gln Ser Gly Ile Asn Gly Ile Leu
```

-continued

```
                   805                 810                 815
Lys Lys Pro Val Ile Leu Gln Glu Leu Lys Asp Glu Leu Ala Arg Ile
            820                 825                 830

Leu Gln Ser Thr
        835

<210> SEQ ID NO 4
<211> LENGTH: 777
<212> TYPE: PRT
<213> ORGANISM: Oryza sativa
<220> FEATURE:
<221> NAME/KEY: misc_feature
<223> OTHER INFORMATION: ETHYLENE RECEPTOR 4 (ETR4) of Oryza sativa
      japonica (RICE)

<400> SEQUENCE: 4

Met Ala Met Val Thr Ala Arg Gln Phe Leu Ala Ser Ala Ala Glu Leu
1               5                   10                  15

Gly Ser Gly Arg Arg Cys Gly Gly Gly Ala Cys Asp Met Arg
            20                  25                  30

Glu Asp Gly Gly Val Glu Ala Leu Met Gln Cys Gln Arg Val Ser Asp
        35                  40                  45

Leu Leu Ile Ala Ala Ser Phe Leu Ser Ile Pro Leu Glu Leu Phe Tyr
    50                  55                  60

Phe Ala Thr Cys Ala Asp Leu Ser Glu Val Lys Cys Ala Val Leu His
65                  70                  75                  80

Phe Cys Ala Phe Ile Val Leu Cys Gly Ala Thr His Leu Leu Ala Ala
                85                  90                  95

Phe Thr His Ala His Pro His Ser Ala Pro Leu Leu Arg Ala Leu Thr
            100                 105                 110

Ala Ala Lys Val Leu Ala Val Ala Ser Ser Ala Ala Ala Val Ser
        115                 120                 125

Leu Leu Thr Phe Ile Pro Lys Leu Leu Arg Ile Lys Val Arg Glu Ser
    130                 135                 140

Leu Leu Arg Asp Lys Ala Ser Arg Leu His Arg Asp Leu Gly Leu Val
145                 150                 155                 160

Arg Arg Arg Glu Glu Ala Thr Ser Arg Ala Val Arg Glu Leu Thr Gly
                165                 170                 175

Arg Ile Arg Ala Ser Pro Pro Asp Ala His Ala Ile Leu Arg Thr Thr
            180                 185                 190

Ala Leu Gln Leu Ala Asp Ala Leu Gly Leu His Ala Cys Ala Val Trp
        195                 200                 205

Met Pro Ala Ala Gly Arg Pro His Asp Leu Val Leu Val His His Leu
    210                 215                 220

Thr Ser Arg Pro Asp Asp Ala Ala Asp Leu Leu Glu Val Gly Asp
225                 230                 235                 240

Ala Cys Thr Val Ala Ala Asp Pro Asp Val Val Asp Val Met Ala
                245                 250                 255

Ser Lys Val Ala Lys Val Leu Gly Pro Asp Ser Ala Leu Ala Met Ala
            260                 265                 270

Ser Ser Val Gly Ala Ala Pro Gly Ala Val Ala Ala Ile Arg Ile
        275                 280                 285

Pro Ile Leu Arg Val Ser Ile Tyr Asp Gly Gly Thr Pro Glu Val
    290                 295                 300

Thr Glu Ala Ser Tyr Ala Ile Leu Val Leu Leu Leu Pro Pro His Asp
305                 310                 315                 320
```

```
Ala Ala Gly Gly Trp Ser Ser His Asp Leu Glu Ile Val Gln Val Val
                325                 330                 335

Ala Asp Gln Ala Ala Val Ala Leu Ser His Ala Ala Val Leu Glu Glu
            340                 345                 350

Ser Arg Ser Met Arg Asp Arg Phe Ala Glu Gln His Arg Ala Leu Met
        355                 360                 365

Gln Ala Lys His Arg Ala Ala Met Ala Thr Arg Ala Phe Ser Ser Ile
    370                 375                 380

Gln Ser Ala Met Cys His Ala Met Arg Arg Pro Val His Ser Val Val
385                 390                 395                 400

Gly Leu Val Ser Met Leu Gln His Pro Glu Ala Asp Thr Met Arg Pro
                405                 410                 415

Glu Gln Arg Leu Ala Val Asp Ala Ile Ala Arg Thr Ser Asn Leu Leu
            420                 425                 430

Ser Ala Leu Met Asp Glu Val Thr Val Asn Arg Gln His Leu Ser Val
        435                 440                 445

Gln Arg Lys Pro Phe Ser Leu His Ala Leu Ile Lys Glu Ala Ile Ser
    450                 455                 460

Val Ala Gly Cys Leu Ser His Cys Gly Gly Ala Gly Phe Leu His Gln
465                 470                 475                 480

Pro Glu Cys Ala Leu Pro Glu Trp Val Gly Asp Glu Arg Arg Val
                485                 490                 495

Phe His Leu Leu Leu Asp Met Val Gly Thr Leu Leu Asn Arg Cys Asn
                500                 505                 510

Thr Gly Ser Gly Ala Cys Arg Leu Ser Phe Ser Val Arg Ile Cys Asn
        515                 520                 525

Val Gly Glu Glu Arg Tyr Ser Leu Asp Trp Ile Pro Met Arg Pro Thr
530                 535                 540

Phe Ser Gly Cys Asn Val Cys Val Lys Phe Lys Val Gly Ile Gly Arg
545                 550                 555                 560

Ser Arg Ser Cys Ala Ile Glu Arg Ser Leu Pro Cys Glu Leu Pro Arg
                565                 570                 575

Arg Ser Ala Ala Thr Thr Ser Ser Gln Met Gly His Ile Phe Ser Gly
            580                 585                 590

Tyr Phe Asn Lys Ile Val Gln Met Met Asn Gly Asn Met Trp Ser Ala
        595                 600                 605

Ser Asp Ser Glu Gly Val Gly Glu Ser Val Thr Leu Ile Leu Gln Phe
    610                 615                 620

Lys Leu Gln Gln Gly His Val Glu Ala Ser Pro Pro Tyr Ile Pro His
625                 630                 635                 640

Leu Asn Gly Leu Arg Val Leu Leu Ala Asp Asp Ala Met Asn Arg
                645                 650                 655

Gly Val Thr Lys Lys Ile Leu Glu Arg Leu Gly Cys Gln Val Met Ser
                660                 665                 670

Ala Pro Ser Gly Ala His Cys Leu Ser Leu Ala Ser Ala Glu Ala
            675                 680                 685

Ser Phe Gln Leu Val Val Leu Asp Leu Asp Asp Arg Ala Val Pro Ser
    690                 695                 700

Ala Ala Met Asp Arg Phe Glu Val Ala Leu Arg Ile Arg Glu Leu Arg
705                 710                 715                 720

Asn Ser Cys Trp Leu Leu Ile Val Ile Ala Val Ala Ala Gly Val Val
                725                 730                 735
```

-continued

```
Ala Thr Asp Asp Gly Gly Ala Val Gln Glu Leu Cys Gln Arg Ala Gly
            740                 745                 750

Ile Asn Gly Leu Val Gln Lys Pro Val Thr Leu Pro Ala Leu Gly Ala
        755                 760                 765

Gln Leu Cys Arg Val Leu Gln Asp Asn
    770                 775
```